(12) United States Patent
Sotolongo

(10) Patent No.: US 11,464,940 B2
(45) Date of Patent: Oct. 11, 2022

(54) SYSTEM AND METHOD FOR BI-DIRECTIONAL FLUID INJECTION

(71) Applicant: Alex Sotolongo, New Haven, CT (US)

(72) Inventor: Alex Sotolongo, New Haven, CT (US)

( * ) Notice: Subject to any disclaimer, the term of this patent is extended or adjusted under 35 U.S.C. 154(b) by 557 days.

(21) Appl. No.: 16/427,732

(22) Filed: May 31, 2019

(65) Prior Publication Data

US 2019/0366035 A1 Dec. 5, 2019

Related U.S. Application Data

(60) Provisional application No. 62/678,286, filed on May 31, 2018.

(51) Int. Cl.
| | | |
|---|---|---|
| *A61M 25/00* | (2006.01) | |
| *A61M 1/36* | (2006.01) | |
| *A61M 25/01* | (2006.01) | |
| *A61M 25/09* | (2006.01) | |

(52) U.S. Cl.
CPC ........ *A61M 25/003* (2013.01); *A61M 1/3659* (2014.02); *A61M 1/3666* (2013.01); *A61M 25/0102* (2013.01); *A61M 2025/0031* (2013.01); *A61M 2025/09008* (2013.01)

(58) Field of Classification Search
CPC .......... A61M 25/01; A61M 2025/0177; A61M 25/0102; A61M 2025/018; A61M 2025/0183; A61M 2025/1045; A61M 2025/0034; A61M 2025/0079; A61M 2025/0175; A61B 2034/301
See application file for complete search history.

(56) References Cited

U.S. PATENT DOCUMENTS

| | | | | |
|---|---|---|---|---|
| 4,774,949 A | * | 10/1988 | Fogarty | A61M 25/01 |
| | | | | 606/108 |
| 6,261,273 B1 | * | 7/2001 | Ruiz | A61F 2/07 |
| | | | | 604/284 |
| 6,494,846 B1 | * | 12/2002 | Margolis | A61M 25/104 |
| | | | | 600/585 |

(Continued)

FOREIGN PATENT DOCUMENTS

| | | | | | |
|---|---|---|---|---|---|
| WO | WO-2019066728 A1 | * | 4/2019 | ......... | A61B 17/3421 |
| WO | WO-2021118933 A1 | * | 6/2021 | ........ | A61M 25/0043 |

*Primary Examiner* — Adam Marcetich
(74) *Attorney, Agent, or Firm* — McCormick, Paulding & Huber PLLC

(57) ABSTRACT

System and method for bi-directional fluid injection includes a retrograde introducer, a retrograde cannula having an inlet opening, intermediate opening and outlet opening, an antegrade introducer and an antegrade cannula. The retrograde introducer is configured to engage with the retrograde cannula and to insert the retrograde cannula into a fluid channel. The antegrade introducer is configured to engage with the antegrade cannula and to insert the antegrade cannula into the fluid channel from within the retrograde cannula through the intermediate opening. After insertion of both cannulas, both introducers are removed. In operation, fluid flows into the retrograde cannula inlet and a portion thereof is diverted to the antegrade cannula which flows the portion in a first direction in the channel, the remainder of the fluid flows out the retrograde cannula outlet in an opposite direction in the channel. The system is removed from the channel using the introducers in reverse order.

16 Claims, 35 Drawing Sheets

(56) References Cited

U.S. PATENT DOCUMENTS

| | | | | |
|---|---|---|---|---|
| 6,726,677 | B1* | 4/2004 | Flaherty | A61F 2/95 604/528 |
| 2001/0003161 | A1* | 6/2001 | Vardi | A61M 25/0116 623/1.11 |
| 2004/0133268 | A1* | 7/2004 | Davidson | A61F 2/915 623/1.35 |
| 2004/0138562 | A1* | 7/2004 | Makower | A61B 6/12 600/439 |
| 2007/0208302 | A1* | 9/2007 | Webster | A61M 25/01 604/103.04 |
| 2007/0293846 | A1* | 12/2007 | von Oepen | A61M 25/0071 604/529 |
| 2008/0009804 | A1* | 1/2008 | Rosetti | A61M 25/0071 604/173 |
| 2008/0228169 | A1* | 9/2008 | Schatz | A61M 25/0169 604/528 |
| 2011/0098561 | A1* | 4/2011 | Thornton | A61M 25/0155 600/431 |
| 2013/0303897 | A1* | 11/2013 | Pursley | A61B 1/3137 600/425 |
| 2015/0011834 | A1* | 1/2015 | Ayala | A61B 17/0218 600/208 |
| 2015/0202360 | A1 | 7/2015 | Chao et al. | |
| 2015/0230951 | A1* | 8/2015 | Al-Saadon | A61F 2/958 623/1.35 |
| 2018/0289926 | A1* | 10/2018 | Haldis | A61M 25/007 |
| 2019/0054230 | A1* | 2/2019 | Al-Jazaeri | A61M 27/00 |

* cited by examiner

SYSTEM AND METHOD FOR BI-DIRECTIONAL FLUID INJECTION

CROSS REFERENCES TO RELATED APPLICATIONS

This application claims the benefit of U.S. Provisional Application No. 62/678,286, filed May 31, 2018, the entire disclosure of which is incorporated herein by reference to the extent permitted by applicable law.

BACKGROUND

Conventional apparatuses and methods for achieving bi-directional fluid injection to inject a fluid in a channel are known. For instance, during cardiopulmonary bypass conventional apparatuses and methods are used to inject blood in a bi-directional manner in a patient's blood vessel. Conventional apparatuses and methods for achieving bi-directional fluid injection fail to adequately generate fluid flow in opposite directions of the channel in which the fluid is injected.

In conventional apparatuses and methods, repurfusion catheters are connected to a bypass circuit at the proximal end of a cannula and additional tubing is required to reach the patient. This poses several problems which increase the risk of failure and long term vascular complications. In particular, blood flowing through a long segment of narrow tubing at high velocities increases the stress on blood products and increases the propensity to clot and obstruct the tubing. Additionally, higher pressures are required to achieve the desired flow rates, which can impair the performance of the circuit. Further, such a technique requires two separate entry points into the blood vessel. Accordingly, it would be desirable to have a device that allows for bidirectional flow while overcoming the shortcomings of other solutions.

DETAILED DESCRIPTION

As discussed in more detail below, in some embodiments, the present disclosure is directed to systems and methods for bidirectional fluid injection. In particular, systems and methods of the present disclosure provides directed flow of a fluid, e.g., oxygenated blood or other fluids, into a target fluid-carrying vessel, e.g., artery or vein or blood vessel, in two opposite directions in the target vessel using a single entry (or puncture) point into the vessel. In some embodiments, it does this by using a main or "retrograde" cannula (or catheter or tube) to receive the input fluid, and having a small or "antegrade" cannula (or catheter or tube), smaller than the retrograde cannula, that exits the retrograde catheter using an exit port (or retrograde cannula intermediate opening) and an elbow socket in the retrograde cannula, and has an output end (or distal end) that is oriented in the opposite direction to the retrograde cannula inside the target vessel. In operation, the antegrade cannula diverts (or taps-off or extracts) a predetermined portion of the fluid flowing in the retrograde cannula to provide directed fluid flow in the target vessel in the opposite direction to the retrograde fluid flow.

Some embodiments of the present disclosure provide elbow socket and antegrade cannula designs, e.g., a seat seal or compression fit, that prevents the antegrade cannula from being released (or lost) into the target vessel, and may provide a fluidic seal between the antegrade cannula and elbow to allow for efficient diversion of fluid from the retrograde cannula into the antegrade cannula.

Systems and methods of the present disclosure also provide introducers to safely and easily insert (or deploy) the retrograde cannula and antegrade cannula into the target vessel, and to safely and easily remove (or extract) the cannulas when the dual flow in the target vessel is no longer needed. In some embodiments, it also allows for insertion of the introducers into the target vessel using guide wires and ultrasound placement/location monitoring for precise placement of the dual flow cannulas into the target vessel. The present disclosure provides a significant improvement over current techniques and devices which require multiple entry points (or punctures) into the target vessel and/or do not provide directed flow in two opposite directions in the target vessel.

Figure 1A:
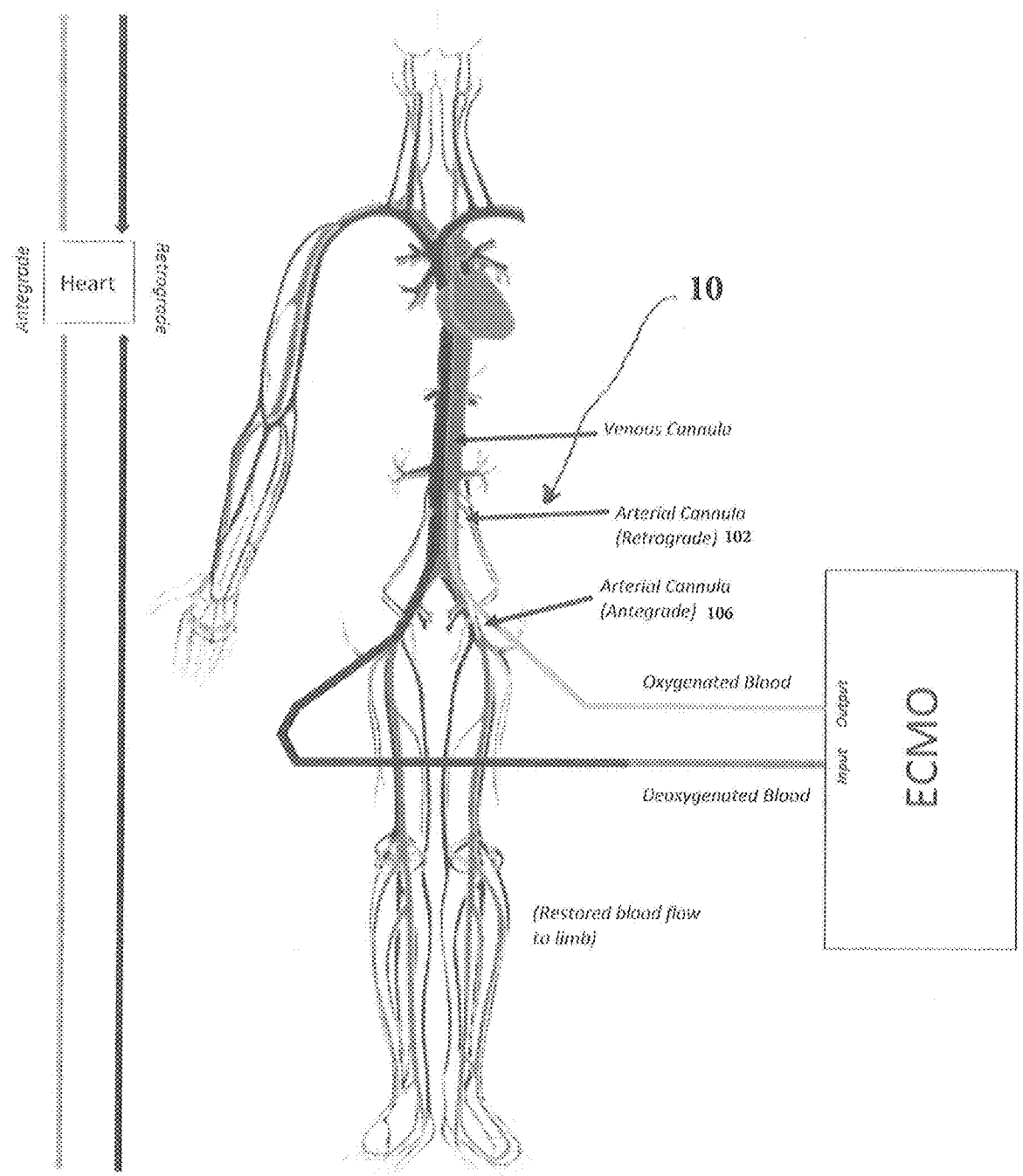
FIG. 1A is a top level diagram showing a bi-directional fluid injection system in accordance with embodiments of the present disclosure.

The nomenclature used herein to describe the cannulas is as follows (and is shown in FIG. 1A, left side): "antegrade" and "retrograde" refer to the directionality of blood being delivered through the cannula. In particular, the "retrograde" cannula directs flow from the leg to the head (opposite the natural flow pattern) and the "antegrade" cannula directs blood from the groin to the leg (in the natural pattern). Also, unless otherwise stated herein, the term "distal" end is where fluid (e.g., blood) exits from, and the "proximal" end is where fluid (e.g., blood) enters.

Referring to FIG. 1A, a top level overview of a system (or assembly) 10 in accordance with embodiments of the present disclosure is shown (once deployed or installed) while in use in a human body and connected to an Extracorporeal Membrane Oxygenation ("ECMO") circuit (or heart-lung machine). In particular, a system and method for bi-directional fluid injection includes a retrograde cannula 102 and antegrade cannula 106 fluidically connected thereto. In some embodiments, in operation, oxygenated blood flows from the ECMO into the retrograde cannula 102 and a portion thereof is diverted to the antegrade cannula 106 which flows the portion in a first direction in the artery (toward the limb), the remainder of the blood flows out of an outlet of the retrograde cannula 102 in an opposite direction in the artery (toward the head and vital organs), thereby providing bi-directional flow in the vessel through a single entry point. As discussed in more detail below, the bi-directional fluid injection (or flow) system is installed into the blood vessel using specially designed introducers and then removed from the vessel using the same introducers in reverse order.

Figure 1B:
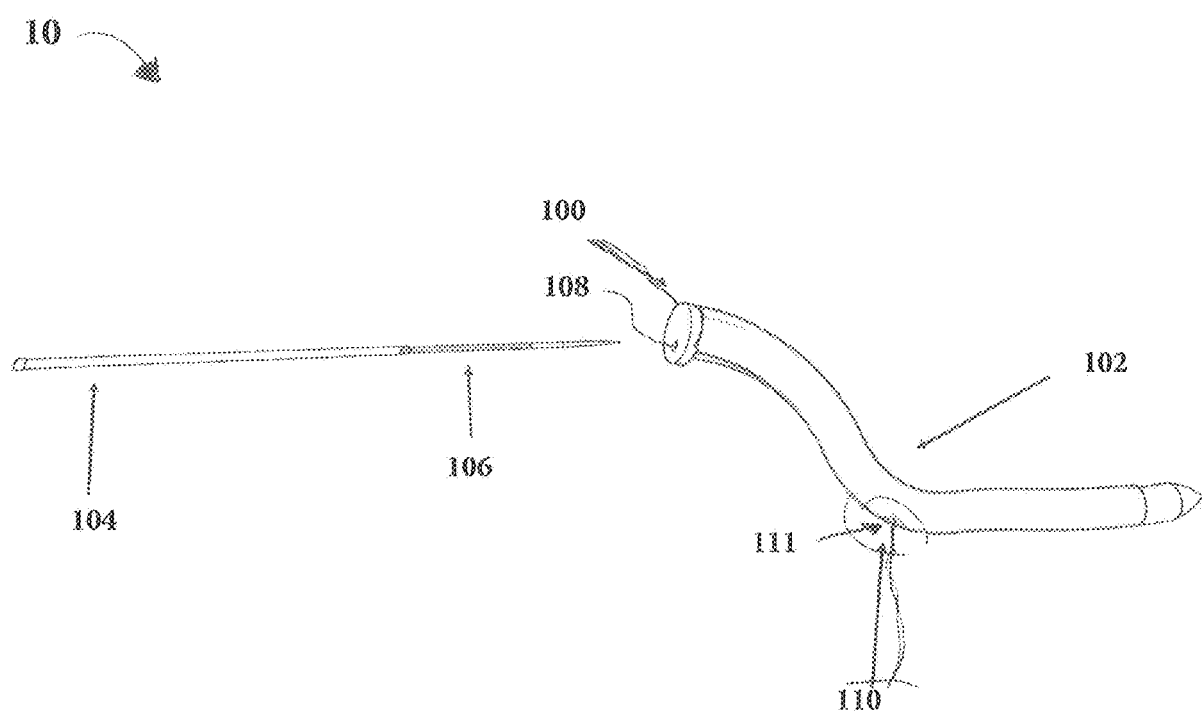
FIG. 1B shows a side perspective view of a bi-directional fluid injection system in accordance with embodiments of the present disclosure.
Figure 1C:
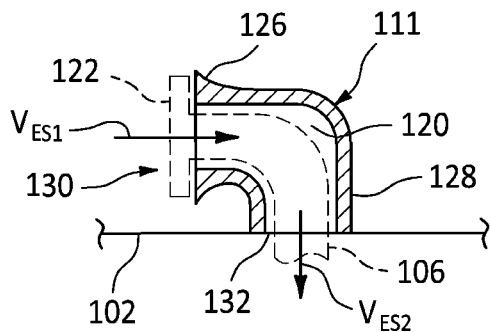
FIG. 1C shows a side view an elbow socket of a retrograde cannula and a portion of an antegrade cannula therein in accordance with embodiments of the present disclosure.
Figure 1D:
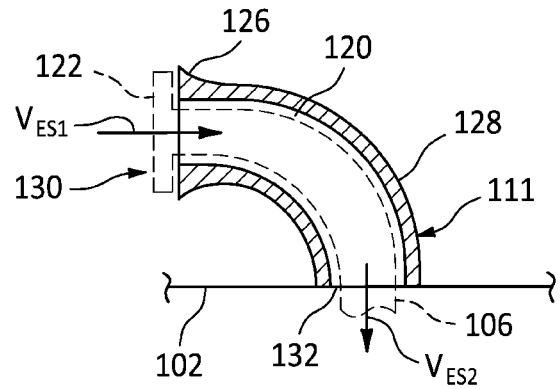
FIG. 1D shows a side view an elbow socket of a retrograde cannula and a portion of an antegrade cannula therein in accordance with embodiments of the present disclosure.

Referring to FIG. 1B, an exemplary bi-directional fluid injection system 10 includes a retrograde introducer 100, a retrograde cannula 102, an antegrade introducer 104 and an antegrade cannula 106. The retrograde introducer 100 is configured to engage with the retrograde cannula 102 in order to introduce the retrograde cannula 102 in a fluid channel such as a blood vessel. The retrograde introducer 100 has a receiving opening 108 configured to receive the antegrade cannula 106 and the antegrade introducer 104. The retrograde cannula 102 has an intermediate opening 110 at an elbow socket 111 configured to permit the passage of the antegrade cannula 106 and/or the antegrade introducer 104.

Figure 1E:
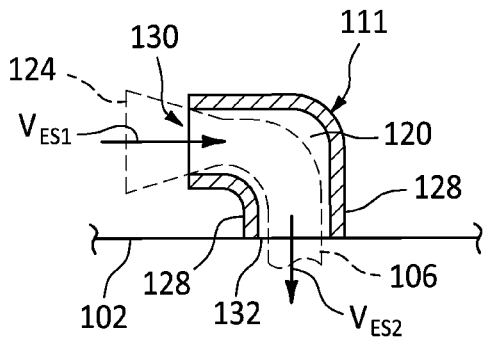
FIG. 1E shows a side view an elbow socket of a retrograde cannula and a portion of an antegrade cannula therein in accordance with embodiments of the present disclosure.
Figure 1F:
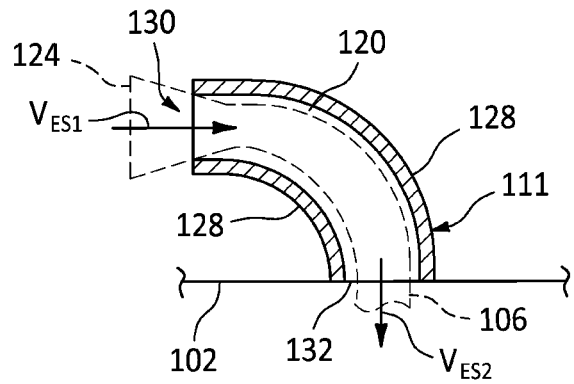
FIG. 1F shows a side view an elbow socket of a retrograde cannula and a portion of an antegrade cannula therein in accordance with embodiments of the present disclosure.
Figure 1G:
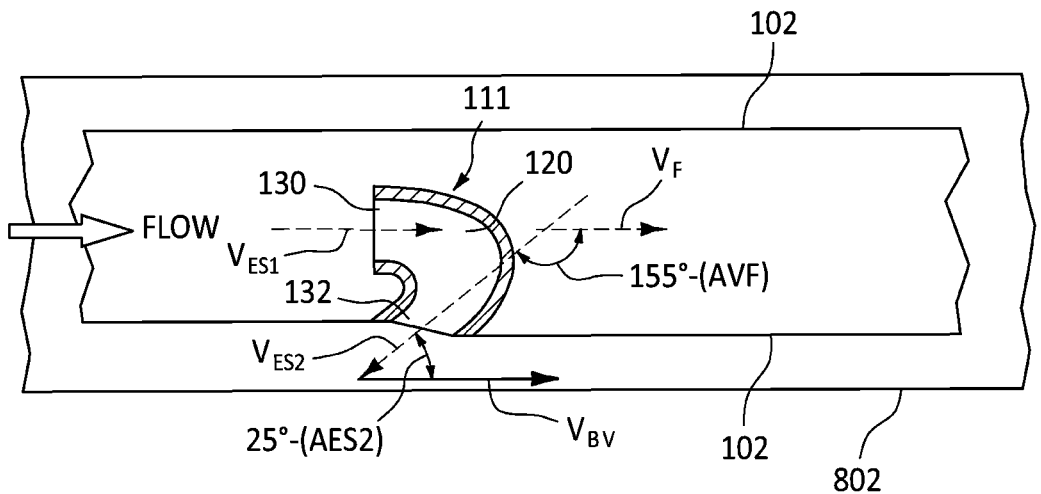
FIG. 1G shows a side view of an elbow socket of a retrograde cannula and a portion of an antegrade cannula therein within a blood vessel in accordance with embodiments of the present disclosure.

Referring to FIGS. 1C, 1D, 1E, 1F and 1G, the elbow socket 111 may be configured as a hollow tube (or channel) 120 having channel walls 128 such that it facilitates proper positioning of the antegrade cannula 106 to maintain correct positioning during use. An entry opening 130 of the elbow socket 111 at the proximal end (closer in a fluid path context to the bypass machine, e.g., ECMO of FIG. 1) may be configured to be approximately perpendicular to the flow through the retrograde cannula 102 and the vector $V_{ES1}$ of the elbow socket tube entry (or longitudinal extension of the entry tube) is initially in line or parallel to the flow vector $V_F$ through the retrograde cannula 102 (e.g. as shown in FIGS. 4A and 7D). A distal end (or exit) 132 may be considered as being closer to the patient in a fluid path context. The path of the tube 120 of the elbow socket tube (or channel) of the elbow socket 111 may include a curve (discussed herein) before exiting through the outer wall of the retrograde cannula 102 shown as an exit vector $V_{ES2}$. Referring to FIG. 1G, in some embodiments, the exit vector $V_{ES2}$ may be offset by an angle AES2, e.g., approximately 25°, from the vector $V_{EV}$ of the target blood vessel and be offset by an angle AVF, e.g., approximately 155°, from a flow vector $V_F$ through the retrograde cannula 102. Other values for AES2 and AVF may be used if desired, provided the resulting system meets the functional and performance requirements described herein. For example, the value of AVF may range from about 90° (shown in FIGS. 1C-1F) to about 180°, which corresponds to values of AES2 of about 90° to 0°, respectively. The tube (or channel) 120 of the elbow socket 111 may include an encasement (or shroud) 111A (FIG. 3B) that improves the hydrodynamic properties of the elbow socket 111, e.g., allowing the fluid flow that is not diverted by the elbow 111 to pass smoothly (with low flow resistance) around the elbow. The entry end 130 may also have a flange or seat 126 which engages with the antegrade cannula 106. The outer diameter of the antegrade cannula 106 (except for the entry end 122,124) is less than that of the tube or channel 120 of the elbow socket 111 so that the antegrade cannula 106 may pass through the elbow socket 111. The most proximal portion (or head or entry portion or entry end) of the antegrade cannula 106 may include a shelf 122 (i.e., flat heat, end cap or flange) or a radial dilation 124 (or tapered radius) that prevents that end portion of the antegrade cannula 106 from passing through the elbow socket 111 (and detaching from the retrograde cannula 102) and may also provide a fluidic seal between the antegrade cannula 106 and the entry 130 of the elbow socket 111, which is discussed in greater detail herein. When the end cap 122 is used, it engages with the seat 126 of the elbow socket 111. When the tapered radius 124 is used, it engages with the inner wall of the tube or channel 120 of the elbow socket 111. Any other technique(s) or structure(s) may be used to ensure that the antegrade cannula 106 is incapable of fully exiting the retrograde cannula 102 through the elbow socket 111 by fully passing through the elbow socket 111 and detaching from the retrograde cannula 102.

Figure 2A:
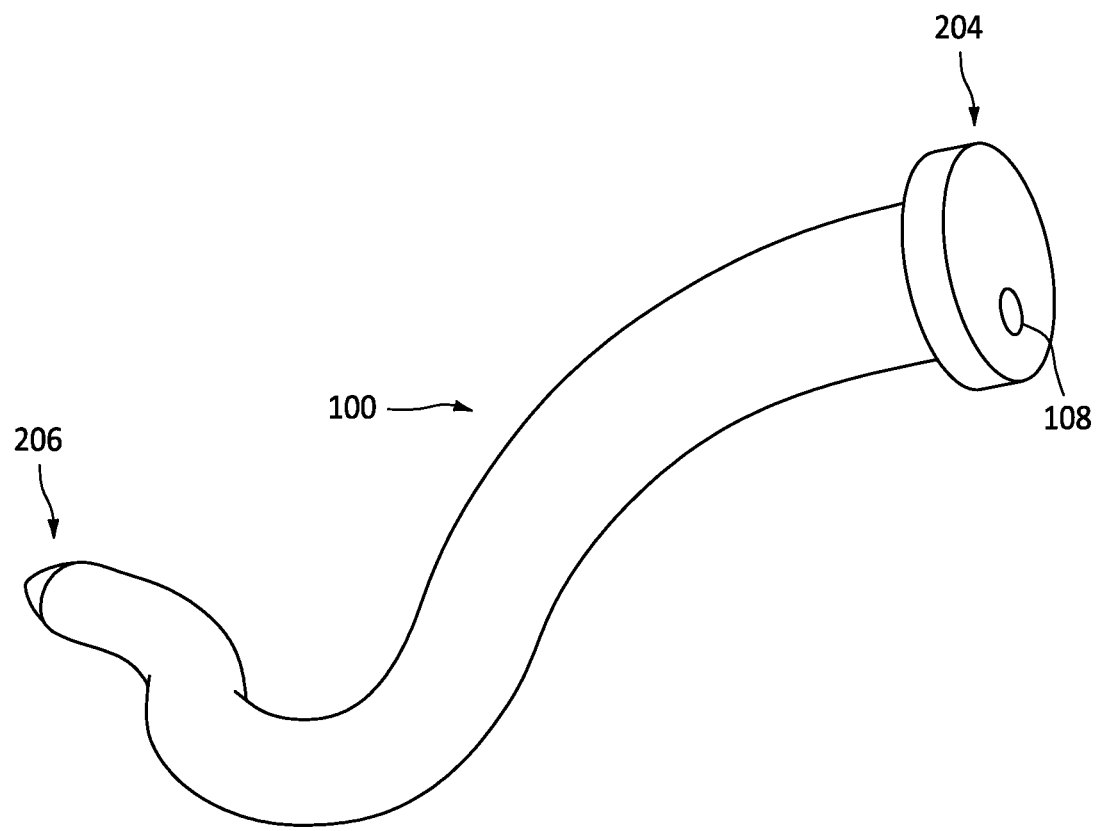
FIG. 2A shows a side perspective view retrograde introducer in accordance with embodiments of the present disclosure.
Figure 2B:
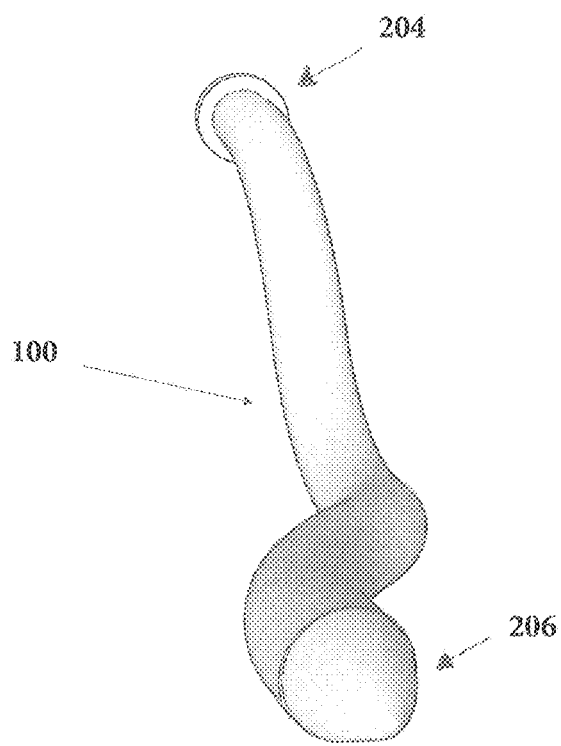
FIG. 2B is an end perspective view of the retrograde introducer of FIG. 2A in accordance with embodiments of the present disclosure.
Figure 2C:
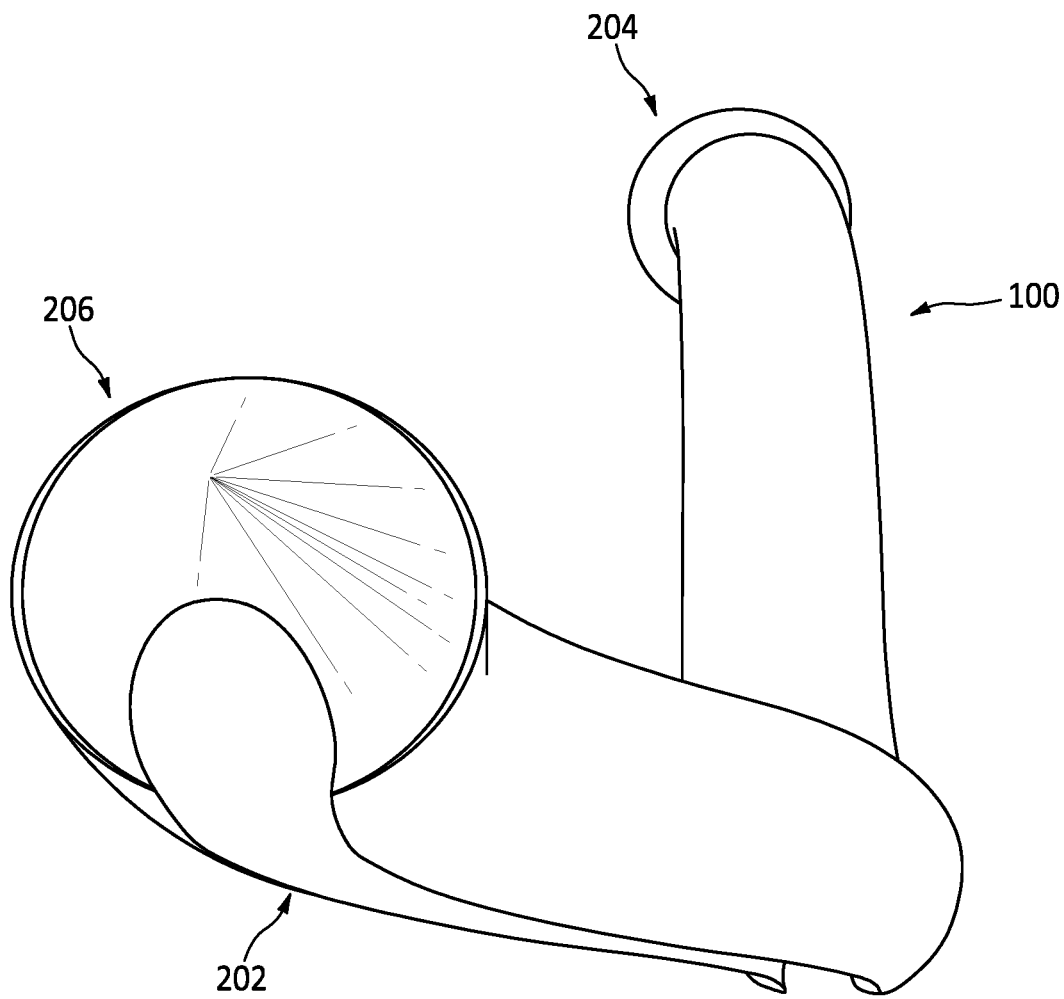
FIG. 2C is another end perspective view of the retrograde introducer of FIG. 2A in accordance with embodiments of the present disclosure.
Figure 2D:
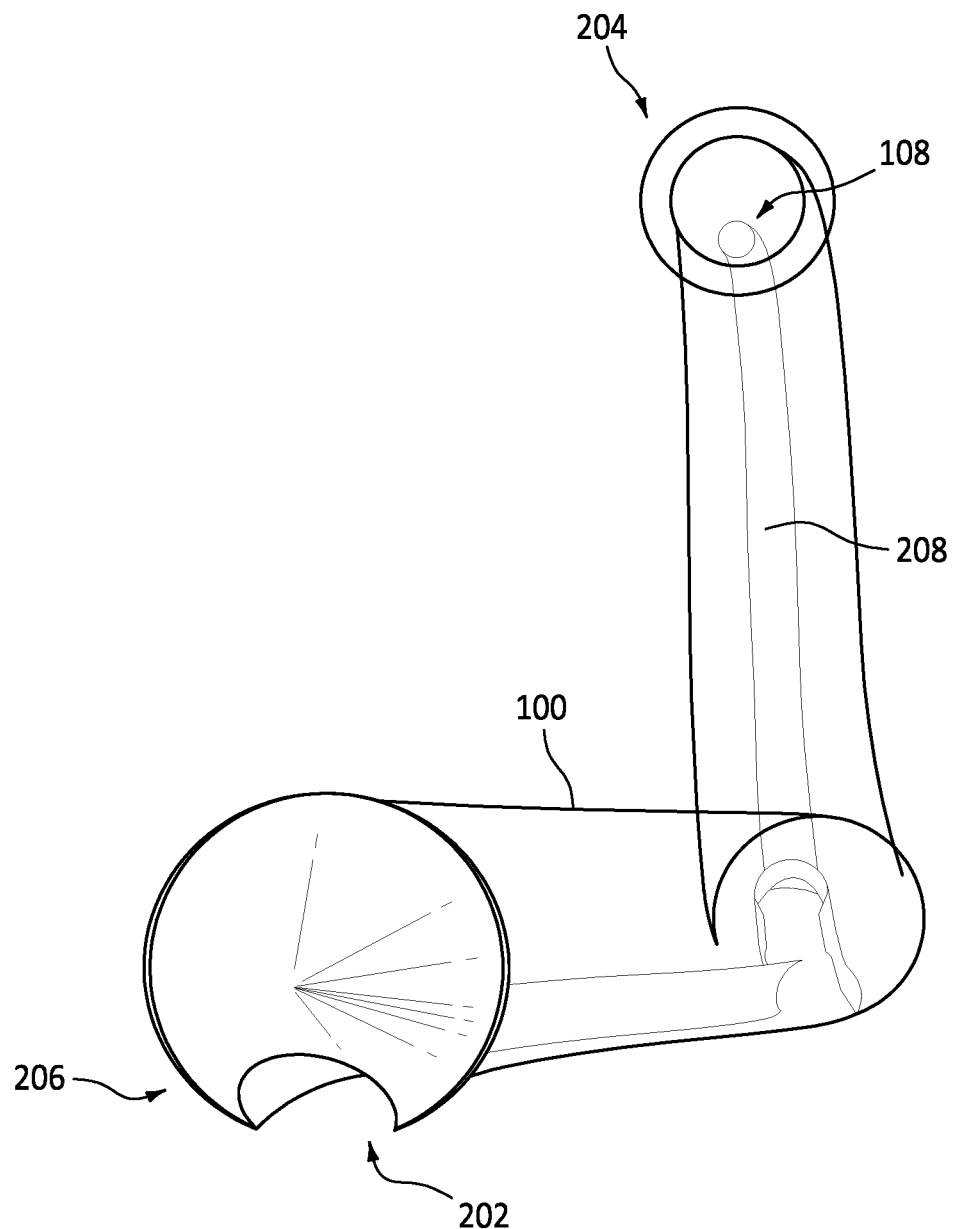
FIG. 2D is a transparent view of the retrograde introducer of FIG. 2C in accordance with embodiments of the present disclosure.
Figure 2E:
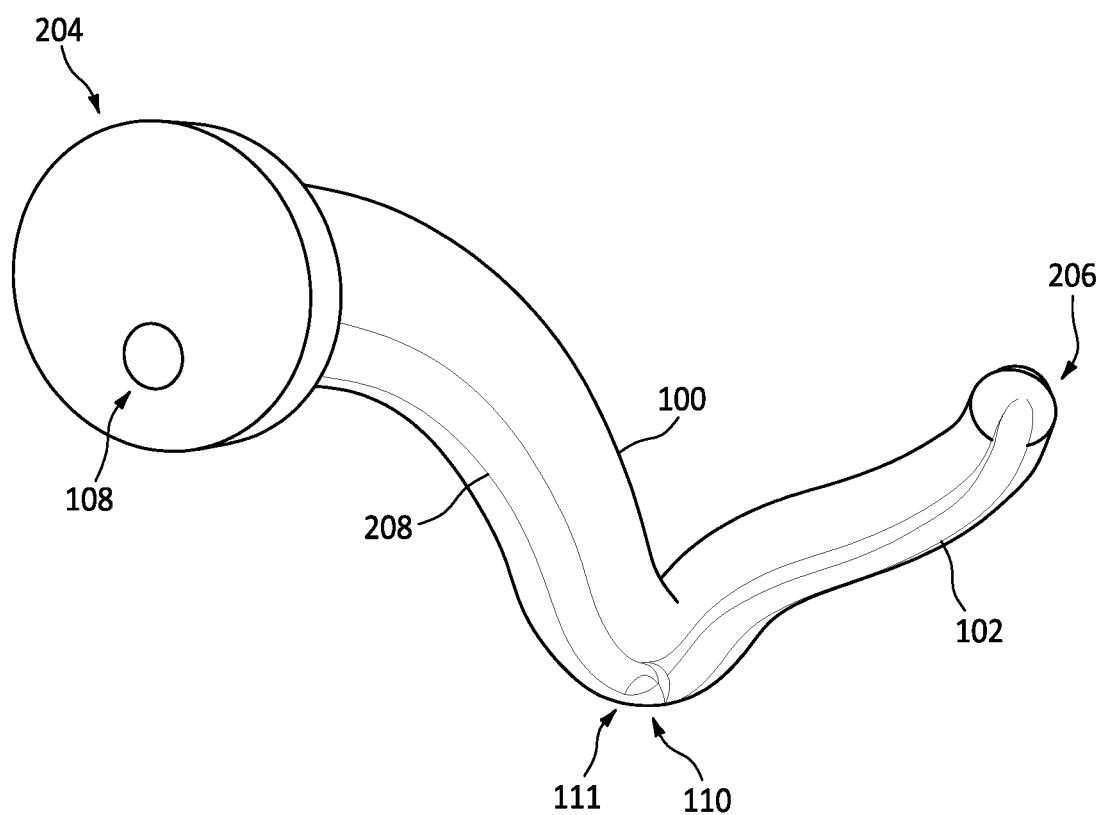
FIG. 2E is a transparent perspective view from an opposite end of the retrograde introducer of FIG. 2D in accordance with embodiments of the present disclosure.
Figure 2F:
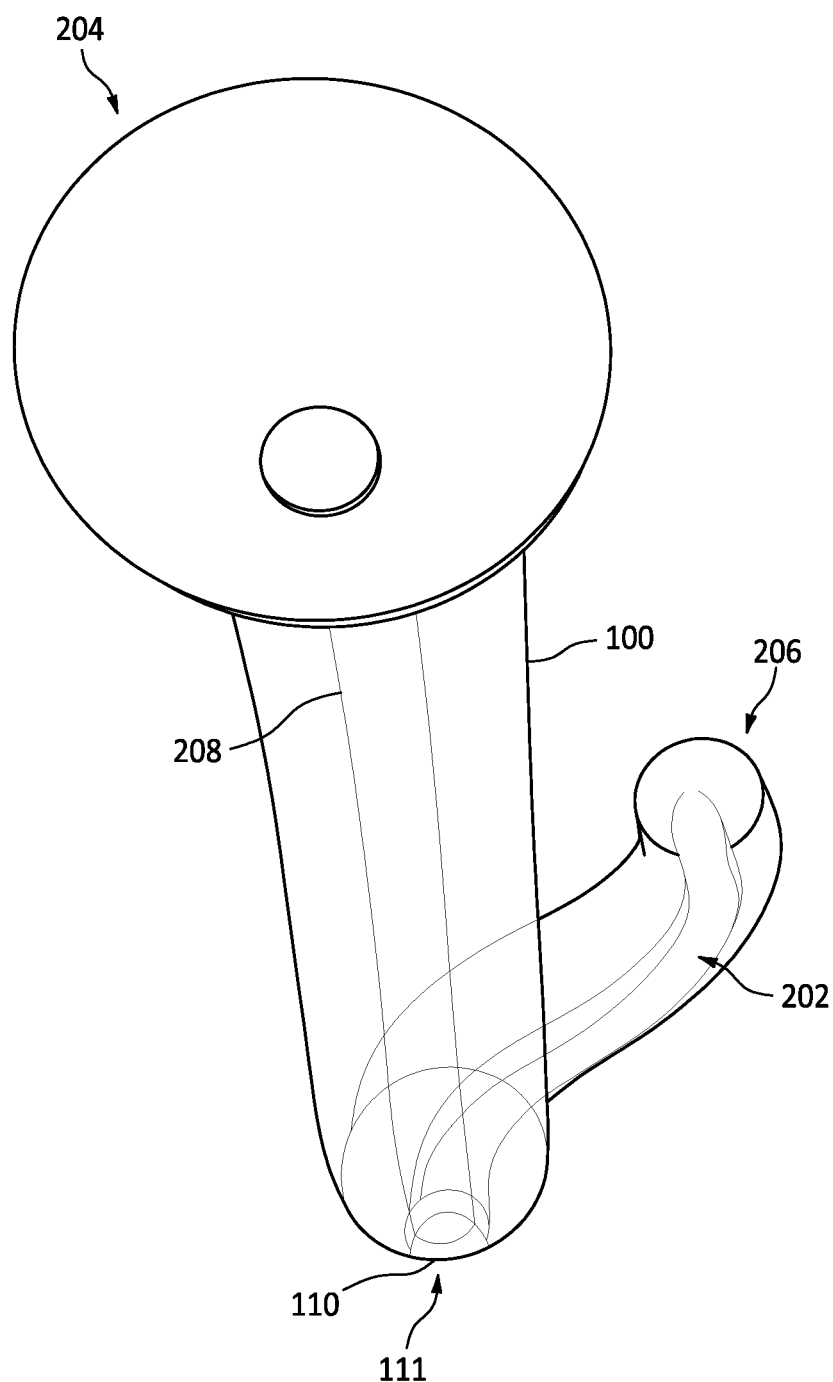
FIG. 2F is a transparent end perspective view of the retrograde introducer of FIG. 2E in accordance with embodiments of the present disclosure.

Referring to FIGS. 2A-2F, the retrograde introducer 100 (FIG. 1) has a elbow socket cut-out passage 202. The retrograde introducer has a proximal (or flat or external) end 204 and a distal (or pointed or internal) end 206. The cut-out 202 extends from substantially near (or adjacent to) the intermediate opening 110 to the distal end 206 of the retrograde introducer 100. The retrograde introducer 100 has an antegrade tunnel 208 (FIGS. 2D, 2E and 2F). The antegrade tunnel 208 extends from the receiving opening 108 to the intermediate opening 110 and/or elbow socket 111.

Figure 3A:
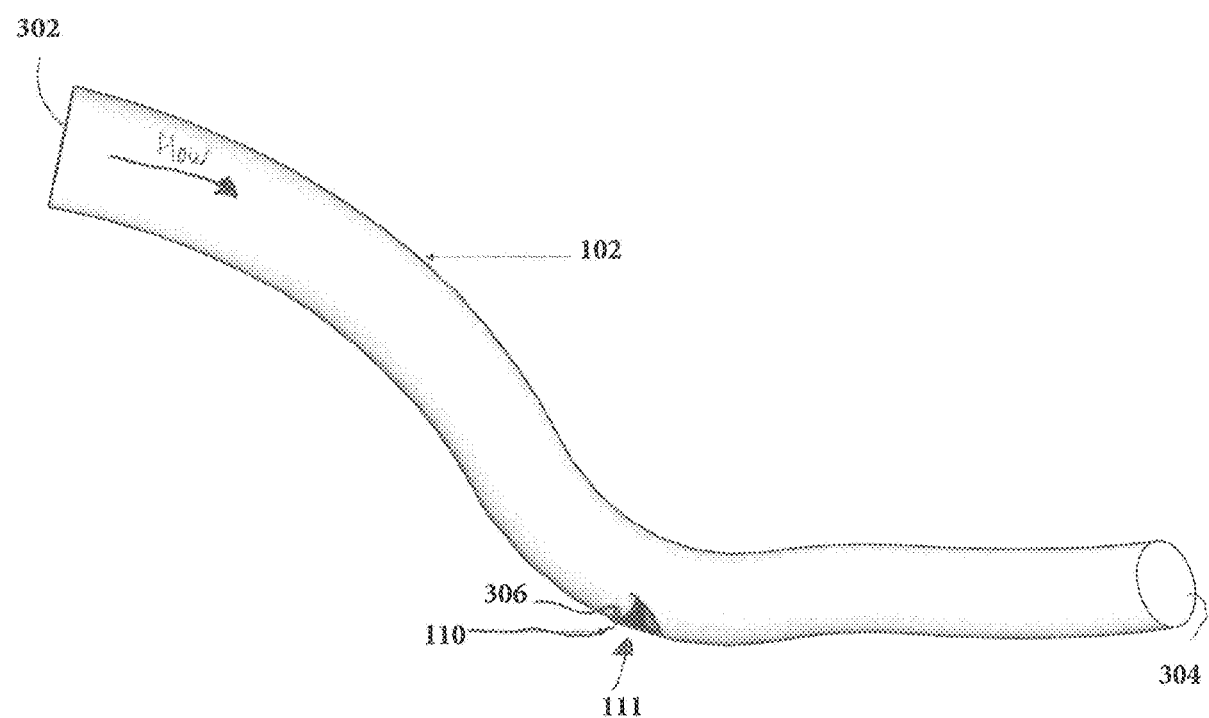
FIG. 3A is a side view of a retrograde cannula in accordance with embodiments of the present disclosure.
Figure 3B:
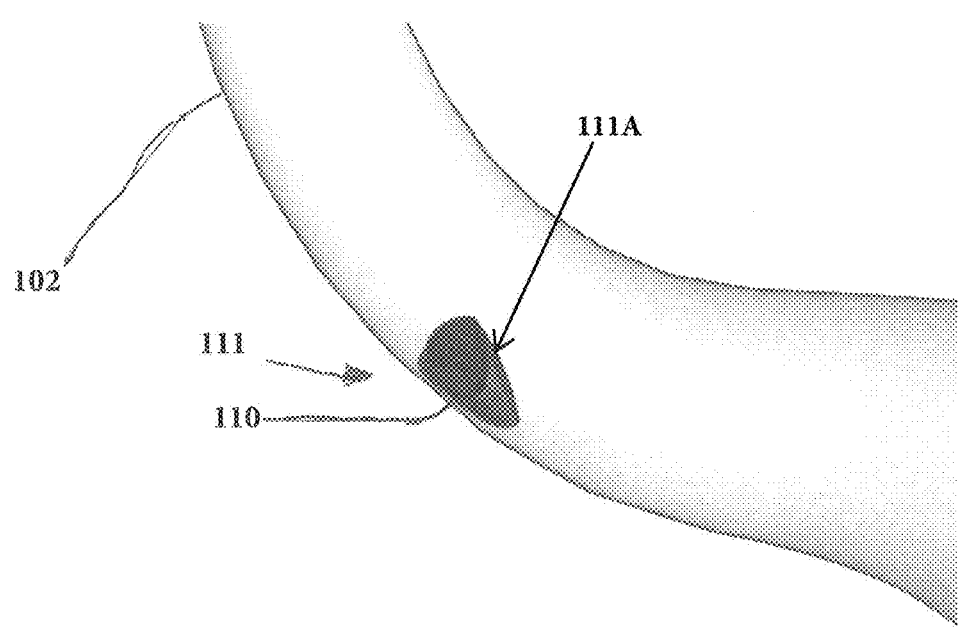
FIG. 3B is a partial, enlarged view of the retrograde cannula of FIG. 3A in accordance with embodiments of the present disclosure.
Figure 4A:
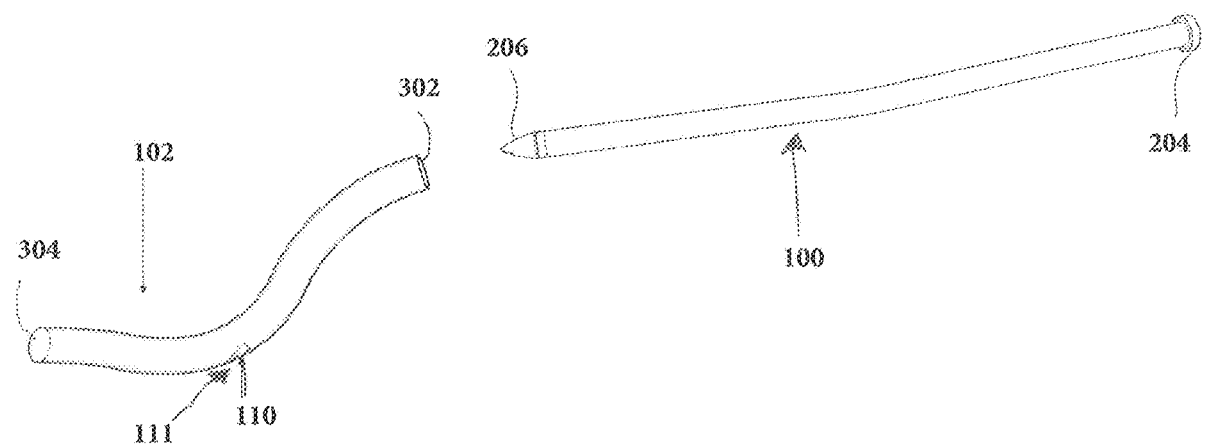
FIG. 4A is a side perspective view of a retrograde cannula and a retrograde introducer of the bi-directional fluid injection system of FIG. 1 in a non-mounted arrangement in accordance with embodiments of the present disclosure.

Referring to FIGS. 3A and 3B, the retrograde cannula 102 (FIG. 1) is shown without the retrograde introducer 100. The retrograde cannula 102 has an inlet opening 302 which receives fluid or blood flow, a main outlet opening 304 and intermediate opening 110, which provides fluid or blood flow. The retrograde cannula 102 has a cannula seat 306, which is later discussed in greater detail.

Figure 4B:
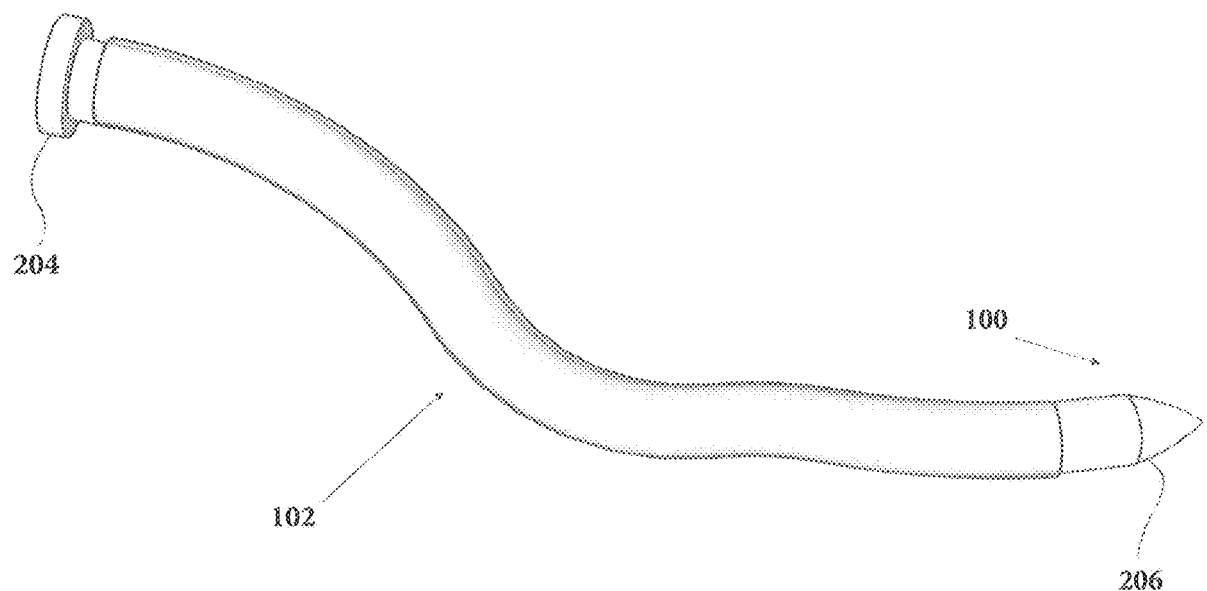
FIG. 4B is a side perspective view of the retrograde cannula and retrograde introducer of FIG. 4A in a mounted arrangement in accordance with embodiments of the present disclosure.
Figure 4C:
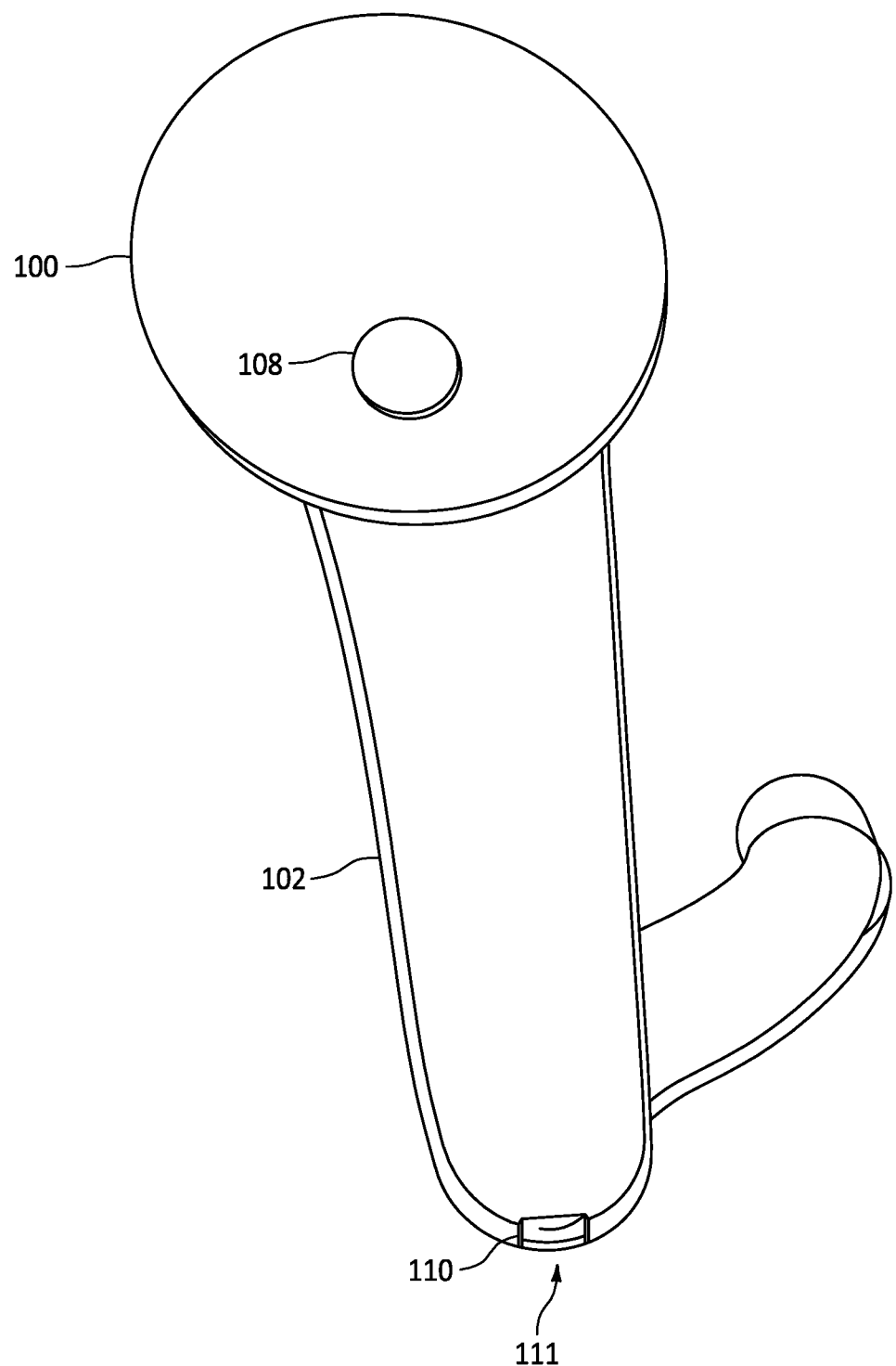
FIG. 4C is an end perspective view of the retrograde cannula and retrograde introducer of FIG. 4B in a mounted arrangement in accordance with embodiments of the present disclosure.
Figure 4D:
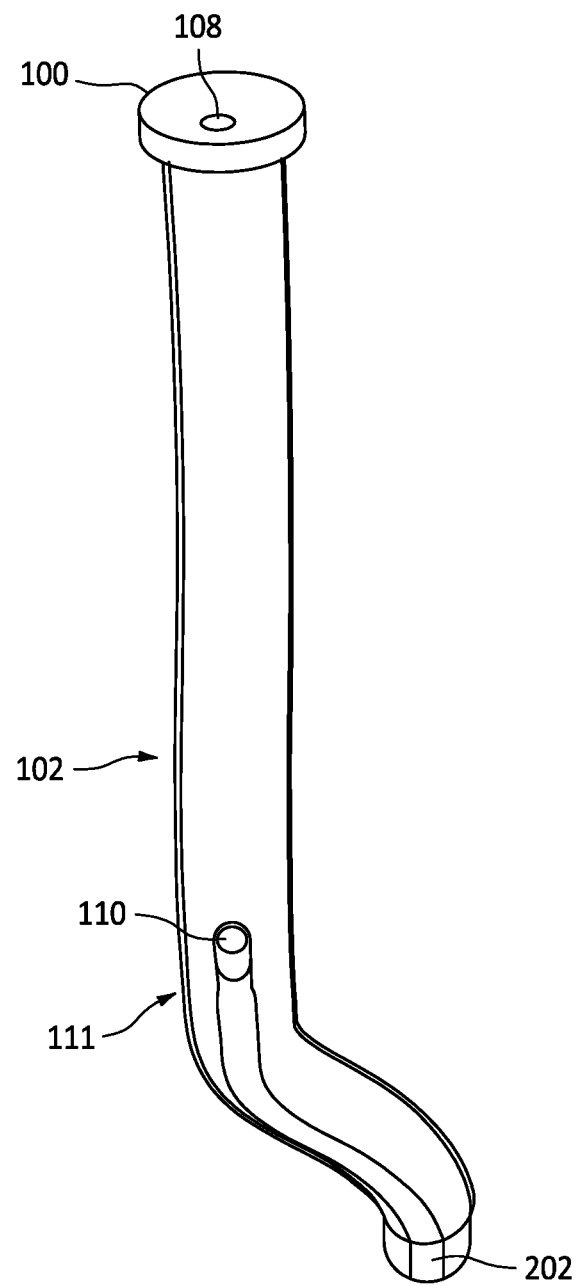
FIG. 4D is a side perspective view of the retrograde cannula and retrograde introducer of FIG. 4B in a mounted arrangement oriented vertically in accordance with embodiments of the present disclosure.

Referring to FIG. 4A, the retrograde cannula 102 (FIG. 1) is shown with the retrograde introducer 100 in a non-mounted arrangement. The retrograde cannula 102 inlet opening 302 is configured to receive the distal end (or pointed end) 206 of the retrograde introducer 100. The retrograde cannula 102 outlet opening 304 is configured to allow the distal end 206 of the retrograde introducer 100 to exit from within the retrograde cannula 102. Referring to FIGS. 4B-4D, the retrograde cannula 102 is shown mounted on the retrograde introducer 100.

Figure 5A:
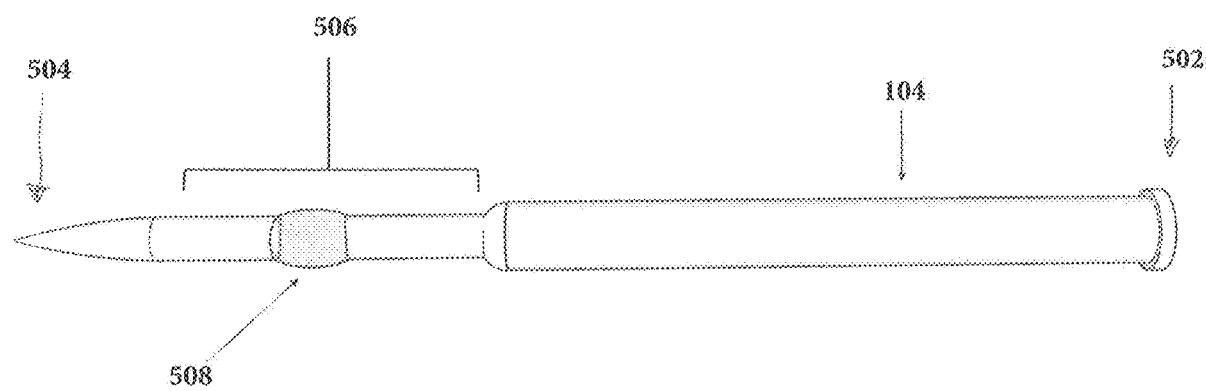
FIG. 5A is a side perspective view of an antegrade introducer in accordance with embodiments of the present disclosure.
Figure 5B:
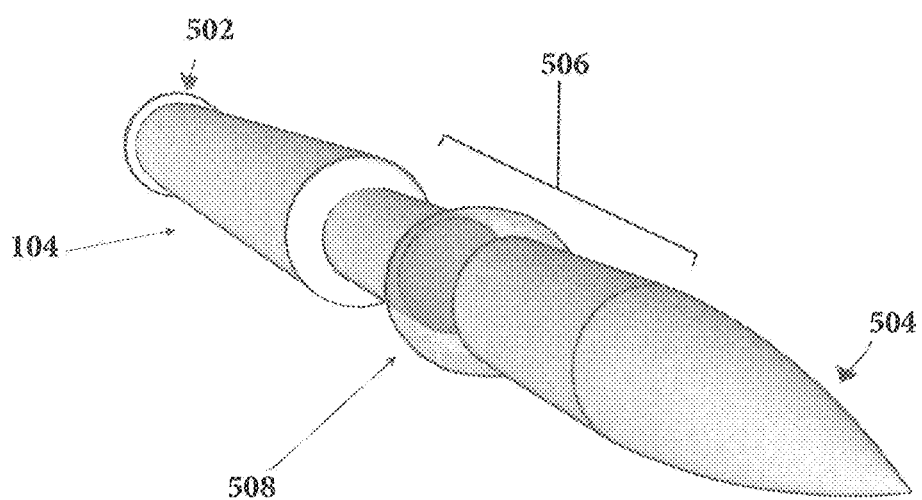
FIG. 5B is a partially transparent perspective view of the antegrade introducer of FIG. 5A in accordance with embodiments of the present disclosure.

Referring to FIGS. 5A and 5B, the antegrade introducer 104 (FIG. 1) has a proximal (or flat or external) end 502 and a distal (or pointed or internal) end 504. The antegrade introducer 104 has a mounting segment 506 including a balloon 508. The mounting segment 506 is configured to be selectively actuated from an engaged position (expanded/inflated) to a disengaged position (flat/deflated), and from a disengaged position to an engaged position. In some embodiments, the balloon 508 of the mounting segment 506 is configured to inflate to an engaged position and deflate to a disengaged position. The balloon 508 (or expandable element) may be controlled through a mechanism including tubing and a valve to be controlled by a user. The tubing is in communication on one end with the interior of the balloon 508 and the other end with a valve (not shown) that allows a user to control a pressure of the balloon 508. When the balloon 508 is inflated, the friction increases between the antegrade introducer 104 and antegrade cannula 106, allowing for coupling of the elements. When deflated, the force is relieved allowing the antegrade introducer 104 to be moved independently from the antegrade cannula 106. Any other technique or structure may be used to engage and disengage the antegrade cannula 106 from the antegrade introducer 104.

Figure 6A:
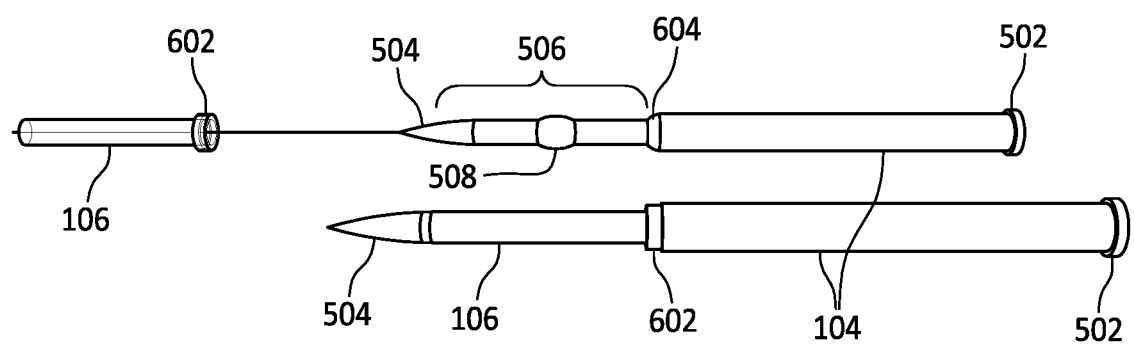
FIG. 6A is a side view of the antegrade introducer of FIG. 5A with an antegrade cannula in a non-engaged arrangement and in an engaged arrangement in accordance with embodiments of the present disclosure.
Figure 6B:
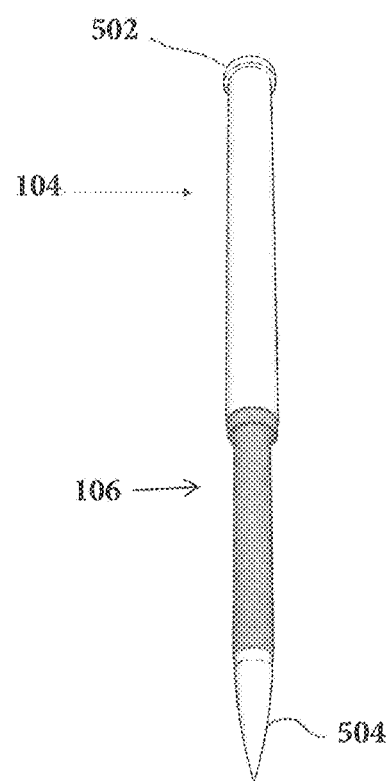
FIG. 6B shows another perspective view of the antegrade introducer and antegrade cannula of FIG. 6A in a mounted arrangement in accordance with embodiments of the present disclosure.

Referring to FIGS. 6A and 6B, the antegrade (or small or limb) cannula 106 (FIG. 1) has a bulged (or enlarged) head (or end cap or flange) 602 at one end. When the antegrade introducer 104 is inserted within the antegrade cannula 106, the bulged head (or flange) 602 rests against an enlarged portion (or stop or seat) 604 of the antegrade introducer 104. The seat 604 is disposed between the proximal end 502 and distal end 504 of the antegrade introducer 104, and the mounting segment 506 is disposed between the seat (or stop) 604 and the distal end 504. When the antegrade introducer 104 is inserted within the antegrade cannula 106, the balloon 508 is configured to engage with the inner surface of the antegrade cannula 106 causing the antegrade cannula 106 to be locked in position when in the engaged position (inflated) and disengage from the antegrade cannula 106 when in the disengaged position (deflated) causing the antegrade cannula 106 to be free sliding such that the antegrade introducer 104 may be selectively engaged (or fixed on) and/or disengaged (or removable) from the antegrade cannula 106.

Figure 7A:
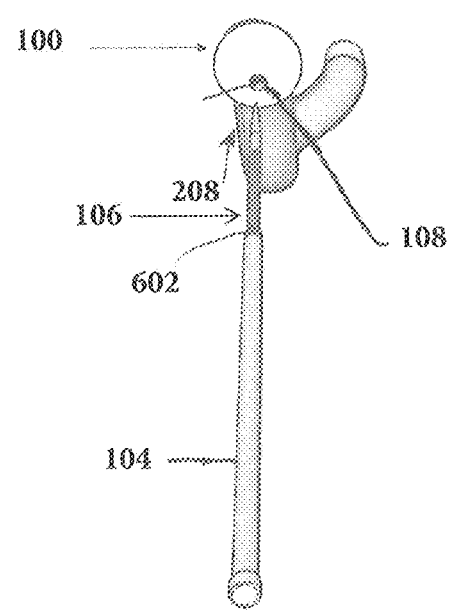
FIG. 7A is an end perspective view of an antegrade introducer engaged with an antegrade cannula prior to insertion into a retrograde introducer and retrograde cannula in accordance with embodiments of the present disclosure.
Figure 7B:
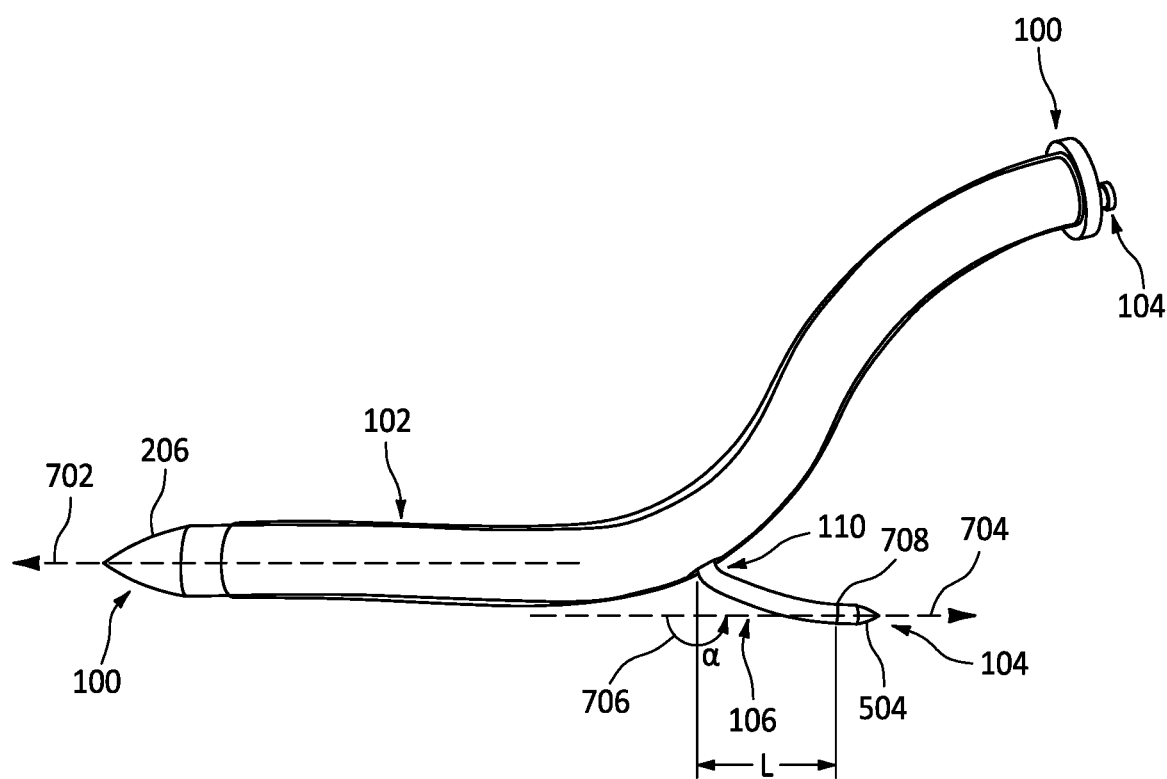
FIG. 7B is a side perspective view of the antegrade introducer engaged with the antegrade cannula of FIG. 7A after insertion into the retrograde introducer and retrograde cannula in accordance with embodiments of the present disclosure.
Figure 7C:
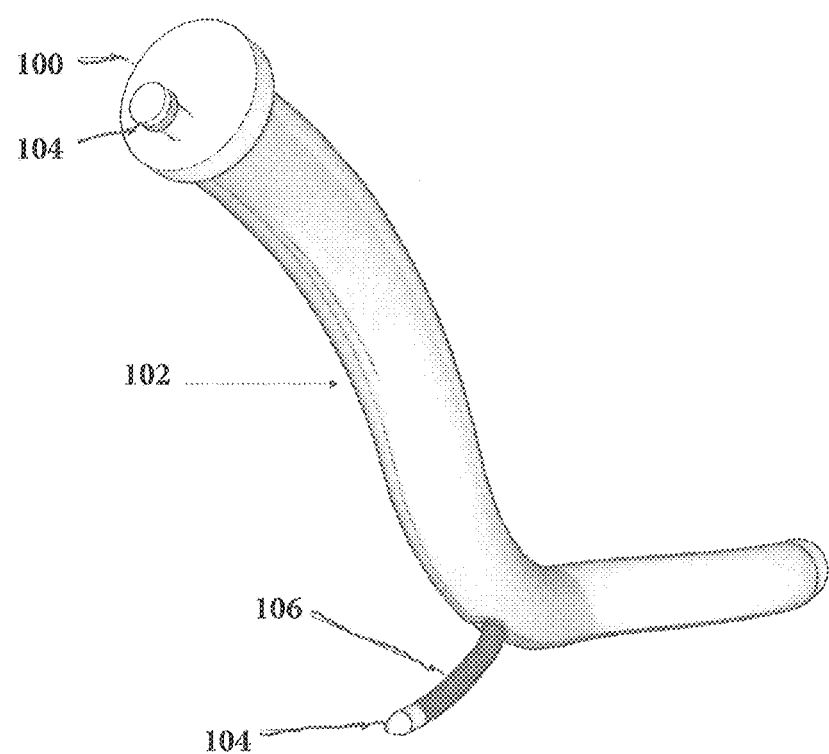
FIG. 7C is an end perspective view of FIG. 7B in accordance with embodiments of the present disclosure.
Figure 7D:
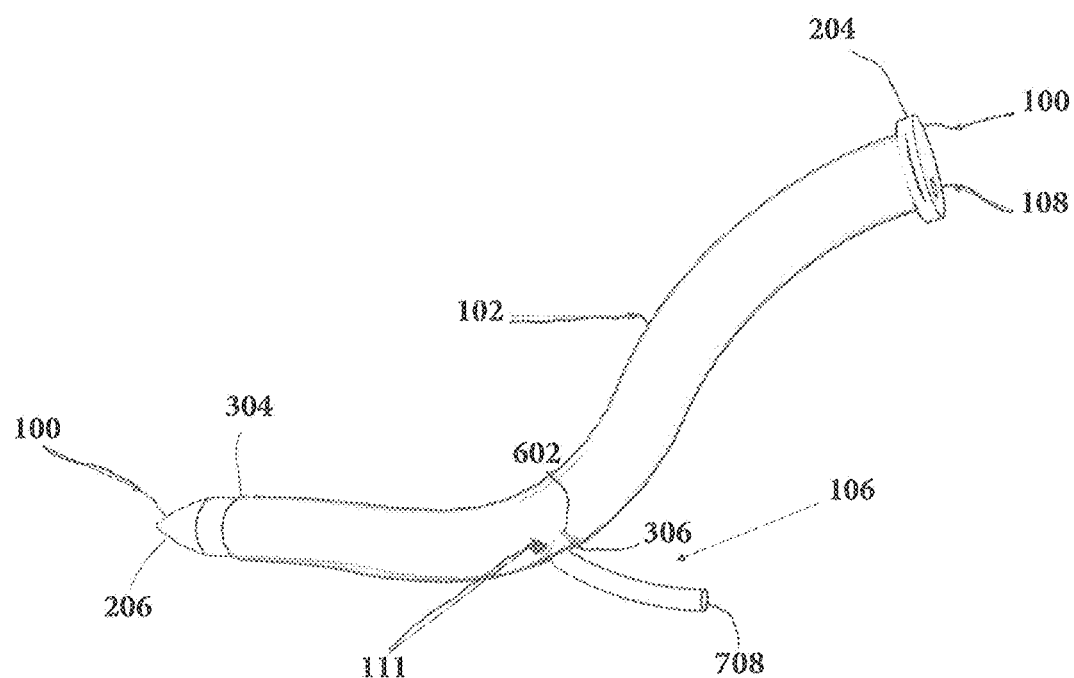
FIG. 7D is a side perspective view of the antegrade cannula of FIG. 7A after insertion into the retrograde introducer and retrograde cannula with the antegrade introducer removed in accordance with embodiments of the present disclosure.

Referring to FIGS. 7A-7C, in operation, the antegrade introducer 104 while engaged with the antegrade cannula 106 (as discussed above) is inserted into the receiving opening 108 and the antegrade tunnel 208 of the retrograde introducer 100. After insertion into the receiving opening 108, the antegrade introducer 104 is moved (or slid) along the tunnel 208—by a user and/or a machine—such that the antegrade introducer 104 and antegrade cannula 106 move through the retrograde cannula 102 and retrograde introducer 100 until the antegrade introducer 104 and antegrade cannula 106 exit the retrograde cannula 102 through the intermediate opening 110. The antegrade cannula 106 is inserted until the bulged head 602 of the antegrade cannula 106 comes to rest on the cannula seat 306 of the elbow socket 111 of the retrograde cannula 102.

Referring to FIG. 7B, the antegrade introducer 104 and antegrade cannula 106 exit the retrograde cannula 102 through the intermediate opening 110 in a direction 704 substantially different and/or opposite to the direction of the longitudinal extension (or axis) 702 of the retrograde introducer 100 and retrograde cannula 102 from the intermediate opening 110 to the distal end 206 of the retrograde introducer 100. In particular, as shown in FIG. 7B, the retrograde cannula 102 extends in a first axial direction 702 that is substantially opposite to the second axial direction 704 of the longitudinal extension of the portion of the antegrade cannula 106 protruding from the intermediate opening 110 outside the retrograde cannula 102, the two directions defining an angle α (706) between them. While FIG. 7B shows the first axial direction 702 differing in direction from the second axial direction 704 by an angle of about substantially 180°, other angles are within the scope of the present disclosure. For instance, the relative angle α between the first axial direction 702 and the second axial direction 704 may be about, without limitation, 150°, 120° or 90° as measured from the first axial direction 702. Other angles may be used provided it provides the desired directed flow from the antegrade cannula into the desired target vessel. The antegrade introducer 104 is inserted into the tunnel 208 (FIG. 2E) until the antegrade cannula 106 is in a desired position or until it presses against the seat 306 of the elbow socket 111 (FIG. 7D). In some embodiments, the antegrade cannula 106 presses against the seat 306 of the elbow socket 111 to provide a fluidic seal and prevent fluid from leaking out of the system where antegrade cannula 106 meets the elbow socket 111. The formation of the fluidic seal is configured to prevent fluid flow from entering the space between an exterior surface of the antegrade cannula 106 and an interior surface of the elbow socket 111 and then exiting through the intermediate opening 110 into the fluid channel and provide high efficiency diversion of flow from the retrograde cannula 102. The desired position may be determined by the values of the angle α and/or a length L of antegrade cannula 106 extension into the fluid channel (or blood vessel) from the intermediate opening 110 of the retrograde cannula 102. In some embodiments, compression fit or interference fit may be used with a tapered antegrade cannula at the proximate end as shown in FIGS. 1E and 1F. Any other technique may be used to provide a fluidic seal at the cannula/elbow socket interface, provided it can be removed or disengaged when needed. In some embodiments, there may be no fluidic seal (or only a partial seal) at the cannula/elbow socket interface, depending on performance requirements.

Figure 7E:
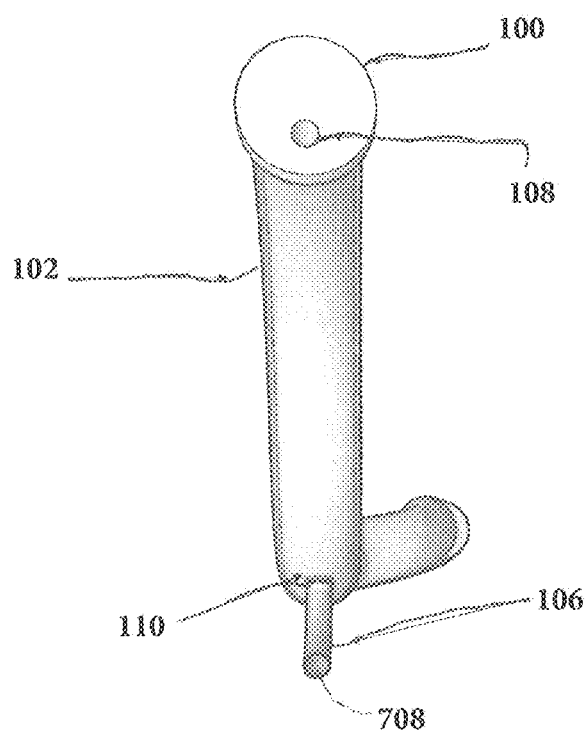
FIG. 7E is an end perspective view of FIG. 7D in accordance with embodiments of the present disclosure.

Referring to FIGS. 7D and 7E, once the antegrade cannula 106 is inserted to the desired position, the mounting segment (e.g. balloon) 506 is actuated to the disengagement position to disengage (or release) the antegrade introducer 104 from the antegrade cannula 106. Once disengaged, the antegrade introducer 104 is withdrawn (or extracted) from the retrograde cannula 102 and retrograde introducer 100 through the tunnel 208 and the receiving opening 108.

Figure 7F:
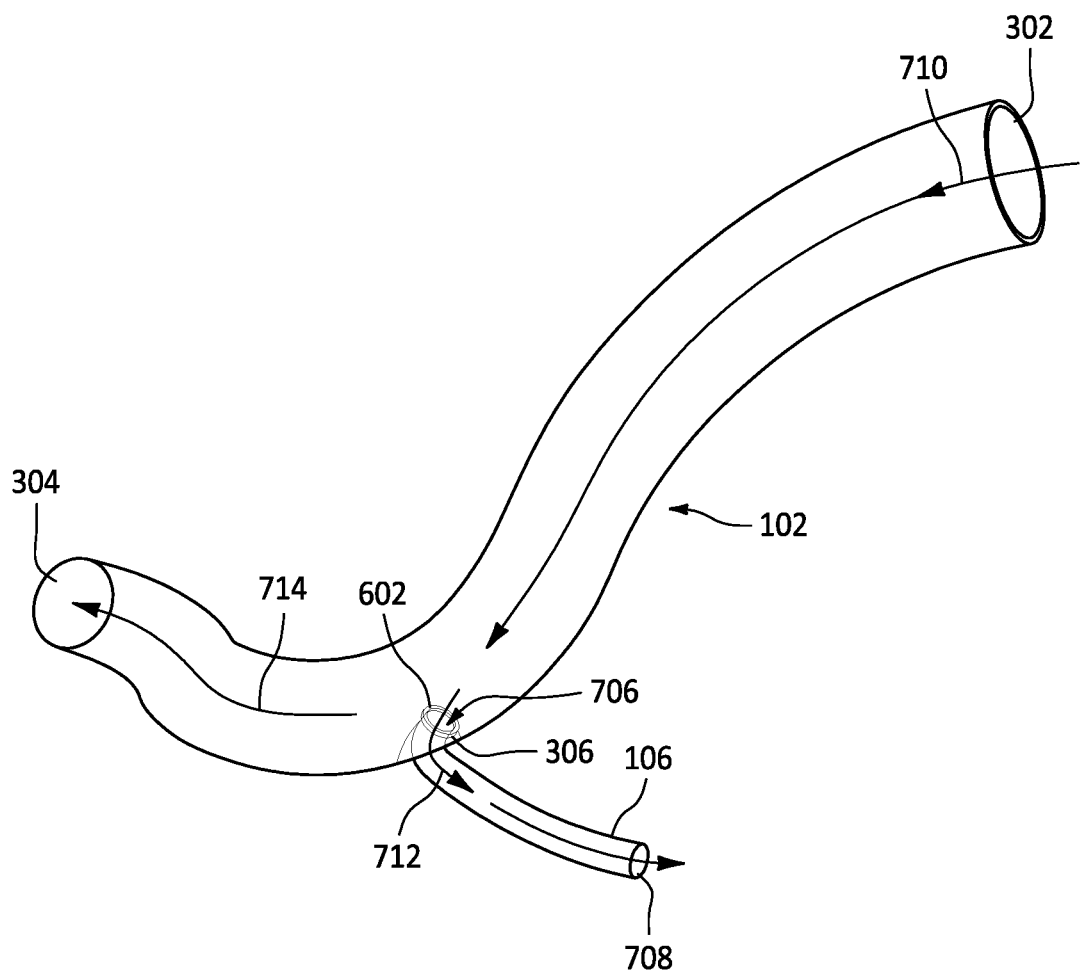
FIG. 7F is a side perspective view of FIG. 7D with the retrograde introducer removed in accordance with embodiments of the present disclosure.

Referring to FIG. 7F, once the antegrade introducer 104 has been removed, the retrograde introducer 100 is withdrawn (or extracted) from the retrograde cannula 102. The cut-out 202 (FIGS. 2C, 2D and 4D) of the retrograde introducer 100 allows for the retrograde introducer 100 to be removed without disturbing or interfering with the position of the antegrade cannula 106. Specifically, the retrograde introducer 100 cut-out 202 is appropriately sized to allow the retrograde introducer 100 to be withdrawn without removing the bulged head (flange) 602 of the antegrade cannula 106 from the cannula seat 306 of the elbow socket 111 of the retrograde cannula 102. The position of the antegrade cannula 106 and the retrograde cannula 102 with the antegrade introducer 104 and the retrograde introducer 100 removed may be referred to as the "deployed position." When in the deployed position, the antegrade cannula 106 has an inlet opening 706 positioned within the retrograde cannula 102 and an outlet opening 708 positioned outside the retrograde cannula 102 and within the fluid channel (not shown in this view).

In the deployed position, fluid 710 may enter the retrograde cannula 102, e.g., from a cardiopulmonary bypass circuit. A portion 712 of the fluid that enters the retrograde cannula 102 will enter the inlet opening 706 of the antegrade cannula 106 and exit at the outlet opening 708 of the antegrade cannula 106 and enter the fluid channel. The remaining fluid 714 will exit the retrograde cannula 102 at the outlet opening 304 and enter the fluid channel. Thus, bi-directional fluid injection is achieved in that one portion of the fluid will enter the fluid channel in the first axial direction 702 (FIG. 7B) and another portion of the fluid will enter the fluid channel in the second (opposite) axial direction 704 (FIG. 7B).

To retrieve the retrograde cannula 102 and the antegrade cannula 106 from the fluid channel (i.e. to perform dual flow device removal), the steps are substantially the reverse of deployment steps discussed above. First, the retrograde introducer 100 is inserted into the retrograde cannula 100 (see FIG. 7D). In embodiments, the retrograde introducer 100 is inserted until the distal end 206 of the retrograde introducer 100 protrudes from the outlet opening 304 of the retrograde cannula 102 and/or the proximal end 204 (or end cap or flange) of the retrograde introducer 100 touches (or is close to) the retrograde cannula 102. Next, the antegrade introducer 104 is inserted into the tunnel 208 of the retrograde introducer 100 through the receiving opening 108 and into the antegrade cannula 106 (see FIGS. 7A and 7B). In some embodiments, the antegrade introducer 104 is inserted until the distal end 504 of the antegrade introducer 104 protrudes from the outlet opening 708 of the antegrade cannula 106 and/or the mounting segment 506 of the antegrade introducer 104 is in a position substantially near the end of the antegrade cannula 106 to engage the antegrade cannula 106 for retrieval and/or the stop (bulged part) 604 of the antegrade introducer 104 hits the end cap or head flange 602 of the antegrade cannula 106.

Once the mounting segment 506 engages the antegrade cannula 106 (as discussed above), the antegrade introducer 104 is withdrawn along with the antegrade cannula 106 through the tunnel 208. In some embodiments, the antegrade introducer 104 and antegrade cannula 106 are withdrawn such that they are entirely removed from the retrograde introducer 100 and retrograde cannula 102. In other embodiments, the antegrade introducer 104 and antegrade cannula 106 are withdrawn such that the antegrade introducer 104 an antegrade cannula 106 are not protruding from the retrograde introducer 100 through the intermediate opening 110. Once the antegrade introducer 104 and antegrade cannula 106 are withdrawn, the retrograde introducer 100 and retrograde cannula 102 are withdrawn from the fluid channel.

Figure 8A:
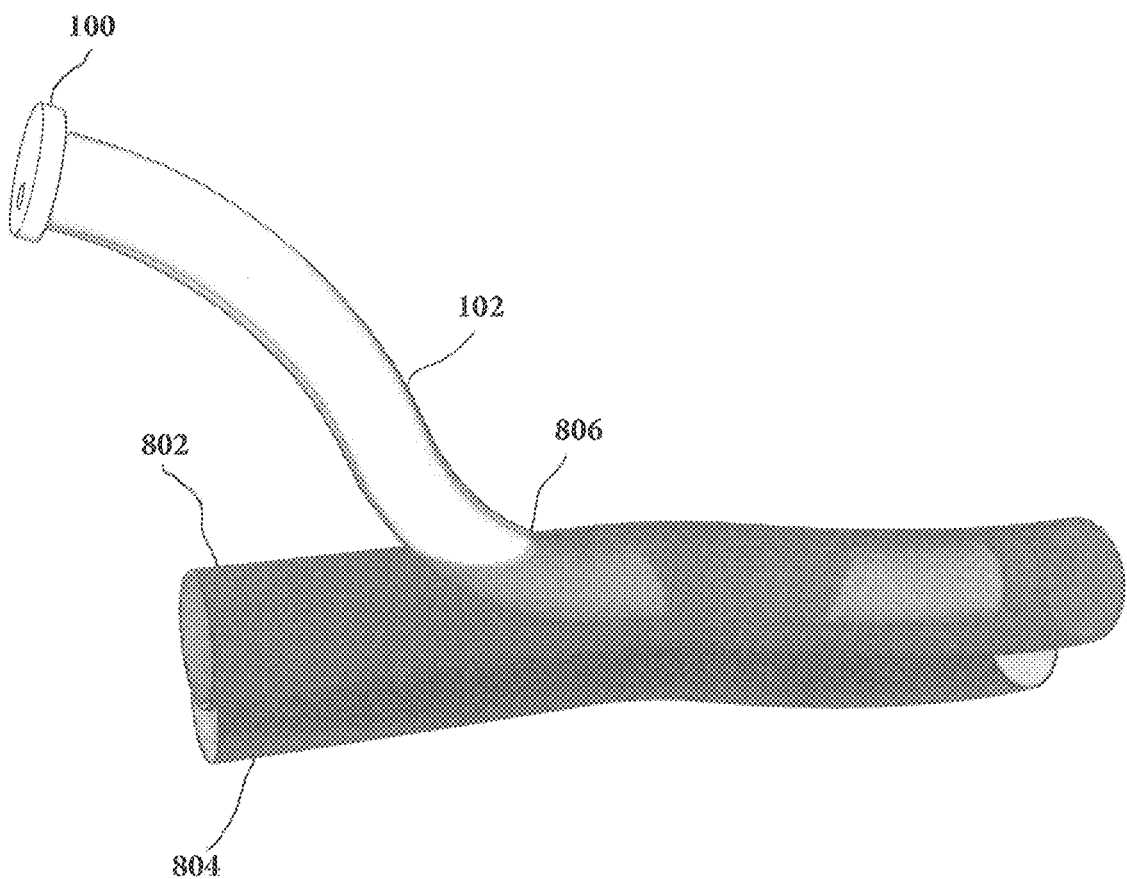
FIG. 8A is a side perspective view of a retrograde introducer and retrograde cannula in a blood vessel of a patient in accordance with embodiments of the present disclosure.
Figure 8B:
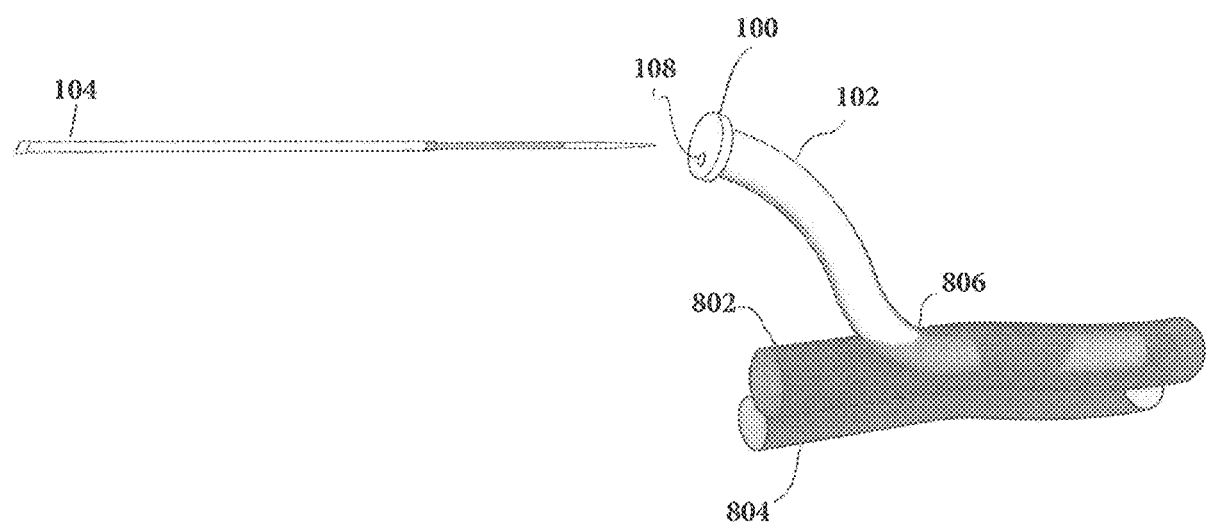
FIG. 8B is a side perspective view of an antegrade introducer and antegrade cannula before insertion into the retrograde introducer and retrograde cannula of FIG. 8A in accordance with embodiments of the present disclosure.
Figure 8C:
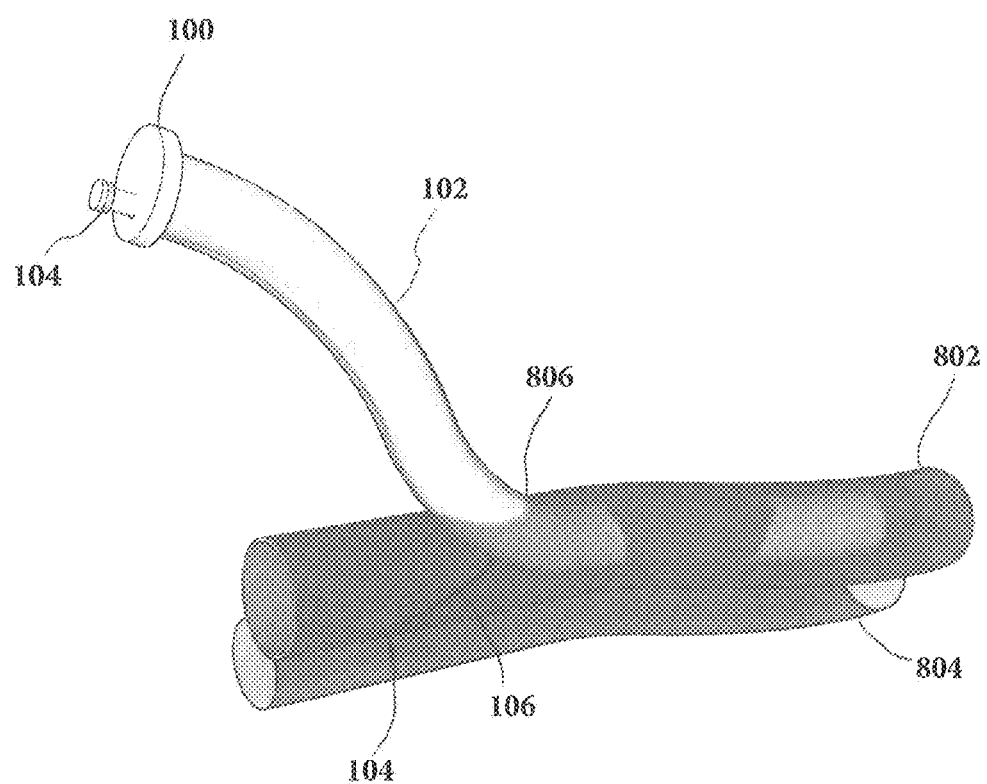
FIG. 8C is a side perspective view of the antegrade introducer and antegrade cannula of FIG. 8B inserted into the retrograde introducer and retrograde cannula of FIG. 8A in accordance with embodiments of the present disclosure.
Figure 8D:
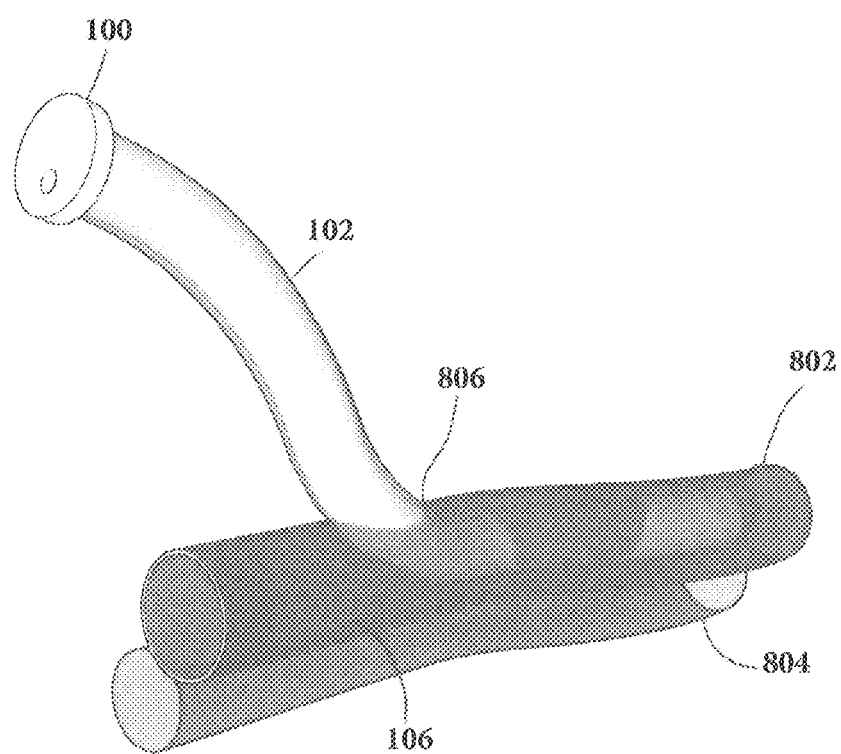
FIG. 8D is a side perspective view of the retrograde introducer, retrograde cannula and antegrade cannula of FIG. 8C with the antegrade introducer removed in accordance with embodiments of the present disclosure.
Figure 8E:
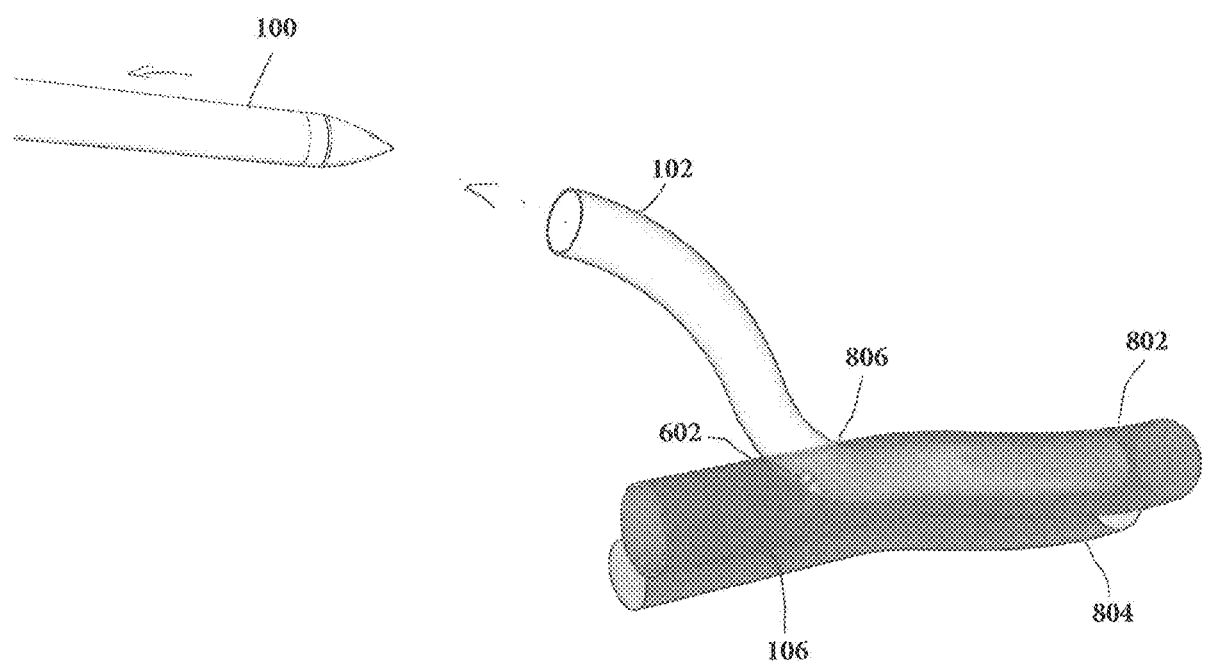
FIG. 8E is a side perspective view of the retrograde cannula and antegrade cannula of FIG. 8D with the retrograde introducer removed in accordance with embodiments of the present disclosure.

Referring to FIGS. 8A-8J, an exemplary depiction of a bi-directional fluid injection system being use to inject blood in a bi-directional manner in an artery (or also known as blood vessel or fluid channel) of a patient is shown. FIG. 8A shows the retrograde introducer 100 and retrograde cannula 102 inserted within an artery 802 of a patient, which rests near a vein 804 of the patient. The artery 802 shown may be a femoral artery of the patient or other blood vessels are within the scope of the present disclosure. The retrograde introducer 100 and retrograde cannula 102 are inserted into the artery 802 through a single puncture entry (or opening) site 806. FIG. 8B shows the antegrade introducer 104 and antegrade cannula 106 before insertion into the receiving opening 108. FIG. 8C shows the antegrade introducer 104 and antegrade cannula 106 inserted such that the antegrade introducer 104 and antegrade cannula 106 are extending in a substantially opposite direction from the retrograde introducer 100 and retrograde cannula 102 (as discussed above with FIG. 7B). FIG. 8D shows the antegrade introducer 104 removed (as discussed above). FIG. 8E shows the retrograde introducer 100 removed from the retrograde cannula 102 (as discussed above).

Figure 8F:
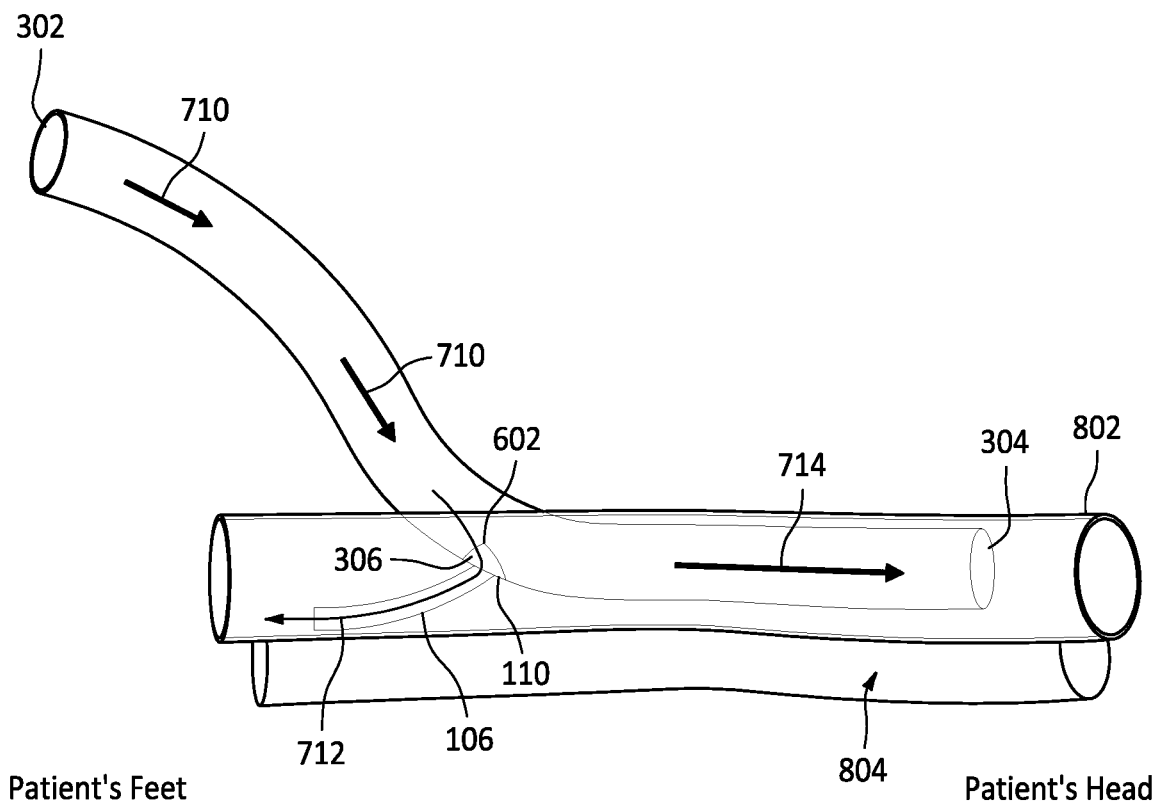
FIG. 8F is a side perspective view of the retrograde cannula and antegrade cannula of FIG. 8E while in use in a blood vessel in accordance with embodiments of the present disclosure.
Figure 8G:
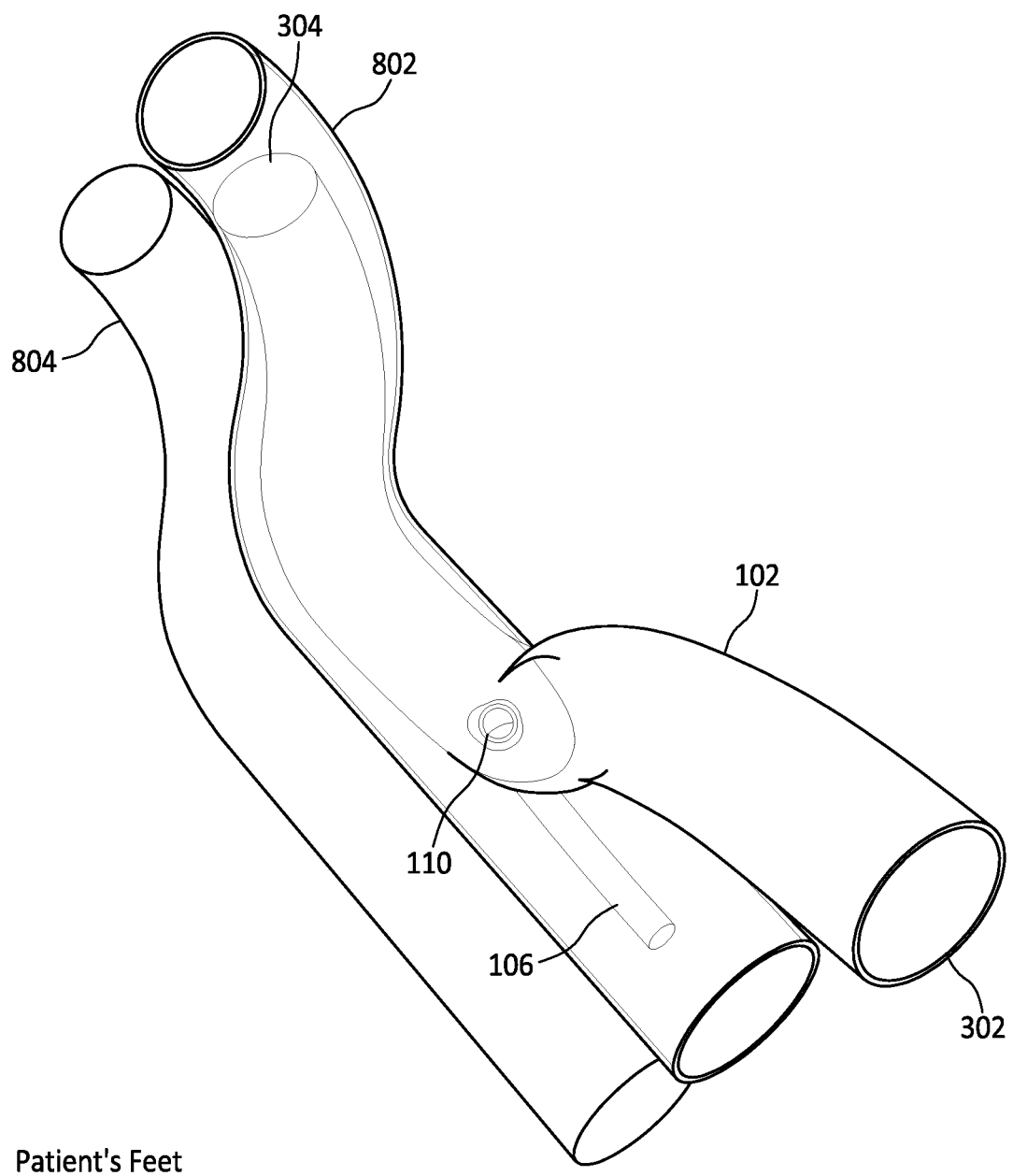
FIG. 8G is a side perspective view of an additional view of the retrograde cannula and antegrade cannula of FIG. 8F while in use in a blood vessel in accordance with embodiments of the present disclosure.
Figure 8H:
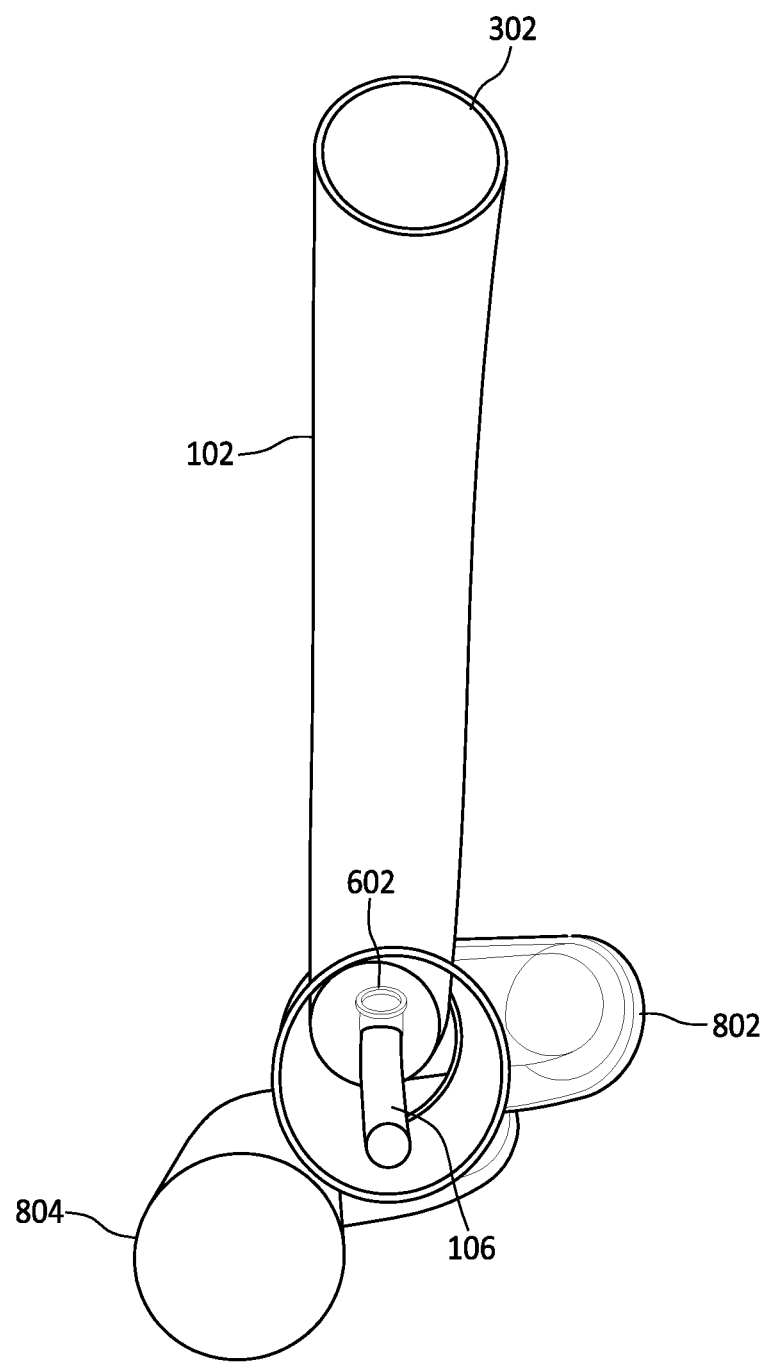
FIG. 8H is an end perspective view of the retrograde cannula and antegrade cannula of FIG. 8F while in use in a blood vessel in accordance with embodiments of the present disclosure.
Figure 8I:
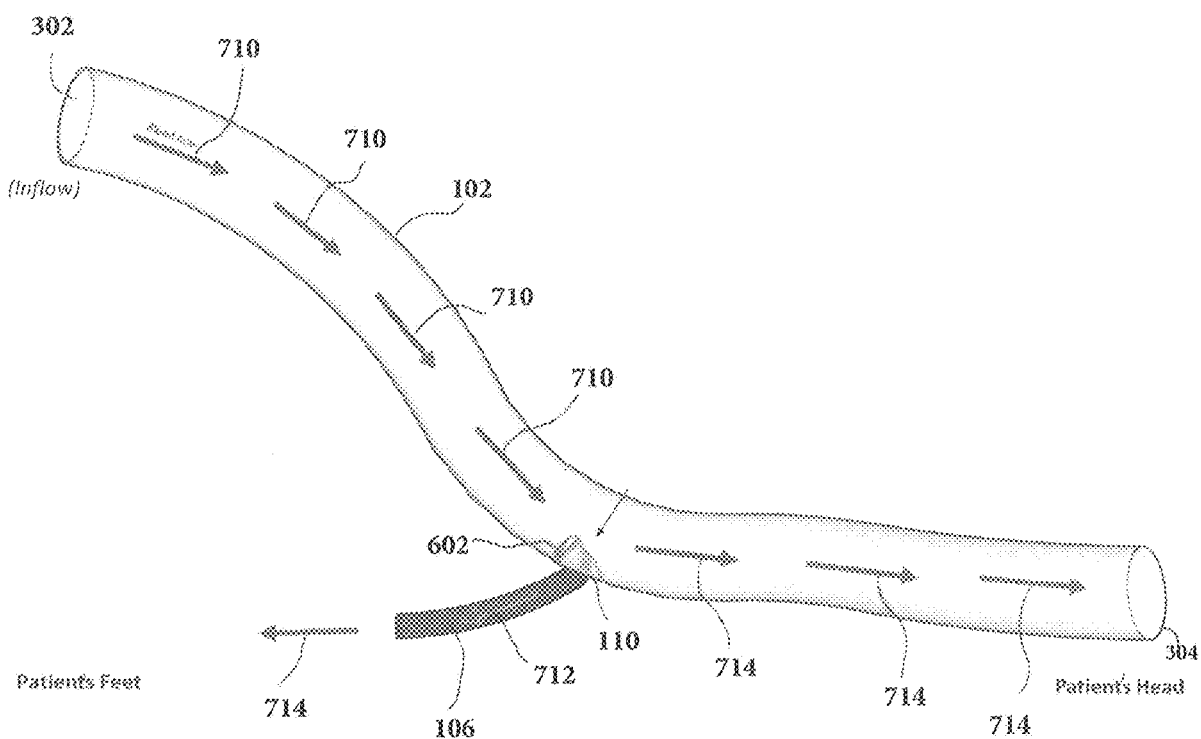
FIG. 8I is a side perspective view of the retrograde cannula and antegrade cannula of FIG. 7F while in use showing blood flow moving through both cannulas in accordance with embodiments of the present disclosure.
Figure 8J:
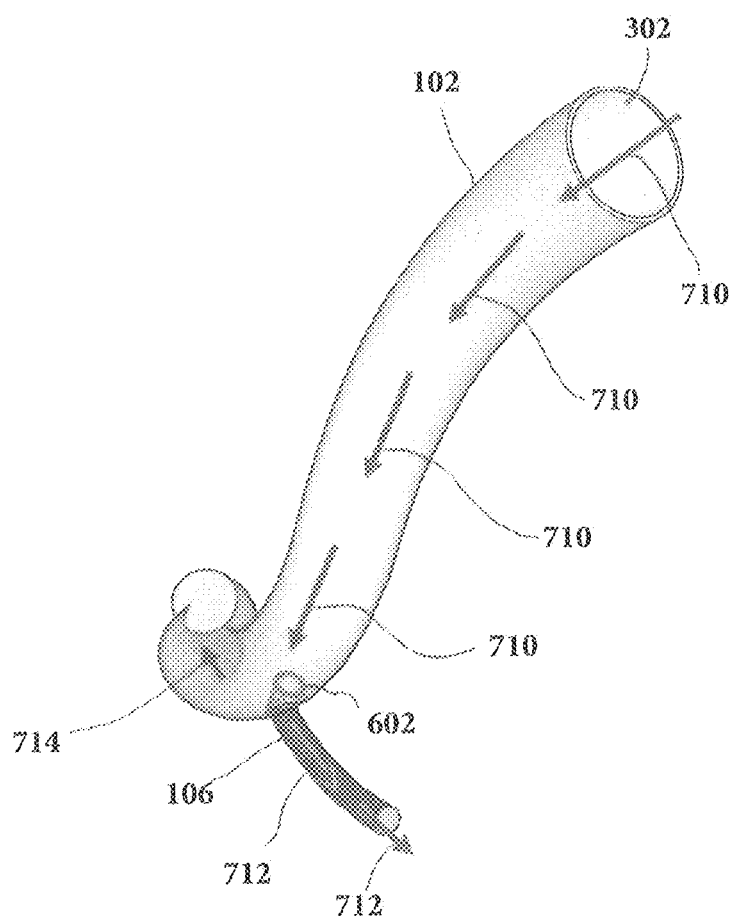
FIG. 8J is a side perspective view of the retrograde cannula and antegrade cannula of FIG. 8I, in accordance with embodiments of the present disclosure.

FIG. 8F shows the retrograde cannula 102 and antegrade cannula 106 in the deployed position and in use while connected with a heart-lung machine (e.g., ECMO, FIG. 1A). While in use, blood flow 710 enters the retrograde cannula 102 at the inlet opening 302 and travels through the retrograde cannula 102 to the outlet opening 304 and into the artery 802. FIGS. 8G and 8H shows additional views of the retrograde cannula 102 and antegrade cannula 106 in the deployed position and in use while connected with the ECMO (FIG. 1A, heart-lung machine). FIGS. 8F and 8I show how, while in use, the input blood flow 808 splits and a portion 712 flows through the antegrade cannula 106 and the remainder 714 flows substantially opposite direction to the blood flow 808 exiting the retrograde cannula 102 (artery 802 omitted from illustration). FIG. 8J shows another view of the input blood flow 808, and the remainder 714 through the retrograde cannula 102 and the portion 712 through the antegrade cannula 106.

In some embodiments, the portion 712 may be about 5-7% (e.g., about 500 cc/min.) of the total input flow diverted. Other amounts may be used for the diversion percentage if desired. The portion 712 of the flow diverted to the antegrade cannula is based on the ratio of the diameter of the retrograde and antegrade cannulas 102, 106 and the relative pressures (or flow resistance) seen at the outputs of the two cannulas 102, 106.

While the mounting segment 506 of the antegrade introducer 104 has been shown and described herein to include a balloon 508 to implement the selective actuation between the engaged position and the disengaged position, other engagement mechanisms known within the art are within the scope of the present disclosure. For example, instead of a balloon 508 (or in addition thereof), the mounting segment 506 may employ, without limitation, engagement mechanisms such as magnets, interlocking shape geometries, latches, claws, barbs, and the like.

In accordance with some embodiments of the present disclosure, the relative angle α between the first axial direction 702 of the retrograde cannula 102 and the second axial direction 704 of the antegrade cannula 106 (namely, a portion thereof as discussed above) is in the range of 90°-180°. In some embodiments, the relative angle is in the range of 120°-180°. In some embodiments, the relative angle is in the range of 150°-180°.

In some embodiments of the present disclosure, the retrograde cannula 102 is composed of a polyurethane, wire reinforced body with an "effective" length of about 7 cm and "true" length of about 20 cm, where the "true" length is the entire length of the cannula, the "effective" length is the portion that is within the target vessel, and is constructed with a diameter in the range of about 18 F-24 F (about 5.3 mm-about 6.7 mm). In embodiments, the exit port 110 is located about 6.5 cm from the tip on the posterior (under) surface of the cannula. The exit port 110 is about 3.3 mm to about 4.7 mm in diameter and is designed to accommodate introduction of the antegrade cannula. The exit port 110 is housed in a slight recess within the cannula wall and contains to create a flushed surface between the junction of the antegrade cannula 106 and retrograde cannulas 102. However, other lengths and diameters are within the scope of the present disclosure.

In some embodiments of the present disclosure, the antegrade cannula 106 has a true length of about 4 cm and an effective length of about 3.9 cm and will be available in diameters ranging from about 12 F-14 F (about 4.0-5.3 mm). The cannula 106 is constructed from polyurethane and is wire reinforced. The proximal end of the cannula contains a dilation measuring about 5 mm lengthwise and a diameter approximately 1.3× that of the antegrade cannula 106. This segment is free of wire reinforcement. Proximal to the bulge there is an about 1 mm segment of normal caliber cannula. At the proximal end there is a circular flange measuring 1 mm from the cannula edge and is wire-reinforced about 2 cm from the proximal end of the cannula are two circular holes measuring about 0.5 mm in diameter and are located substantially 180 degrees from one another on the same plane. However, other lengths and diameters are within the scope of the present disclosure.

In some embodiments, the introducer for the antegrade cannula has a true length of about 21 cm and a diameter ranging from about 3.8 mm to about 5.1 mm with a tapered distal end. Also, about 3 cm from the tip there may be two spring loaded deployable barbs that are designed to engage the holes in the antegrade cannula 106 to hold or lock the antegrade cannula 106 in place (instead of the balloon). Because the antegrade introducer has a tapered (or pointed) distal end or tip, it allows the antegrade cannula 106 and introducer to enter the target vessel at an angle to the vessel wall and then allows the tapered tip to direct the introducer along the wall of the target vessel without damaging the wall of the target vessel.

In embodiments according to the present disclosure, the cannulas 102, 106 can be deployed with a known Seldinger technique (guide-wire insertion) or other introduction techniques. When the cannula is deployed to the effective length, the exit port will be within the lumen of the artery and roughly orthogonal to the course of the artery and retrograde cannula. When the exit port 110 enters the lumen of the target vessel, blood will pulsate through the indicator channel demonstrating that the exit port is entirely within the vessel and, as such, it is safe to deploy the antegrade cannula into the target vessel. Deployment of the antegrade cannula 106 occurs through the guided track (or tunnel 208, FIGS. 2D and 2F) tunneled within the core of the retrograde introducer 100. A wire is first passed through the guided track and passed into the target artery. After confirmation that the guide-wire is correctly positioned by sonography (e.g., using a localized ultrasound probe or the like), the antegrade cannula 106 and introducer are loaded onto the wire and deployed through the guided track with the introducer barbs in the deployed position. The cannula is advanced until the bulge reaches the exit point at which gentler pressure is applied downward forcing a conformational change in the outpouching allowing for antegrade cannula 106 to be fully deployed through the exit port 110. At this point, the bulge will be fully beyond the exit port and within the target artery and the cannula is secured from forward motion by the flange and in the reverse direction by the bulge. The barbs within the introducer are then retracted and the antegrade cannula is disengaged. The introducers are then removed in succession (as discussed herein).

In some embodiments according to the present disclosure, a removal mechanism may include, when the cannula system is removed, the antegrade cannula 106 being first withdrawn to avoid injury to the vessel. The retrograde introducer 100 is first deployed into the retrograde cannula, after which the antegrade introducer 104 is deployed along the guided track and into the antegrade cannula. When the introducer is in the proper location the barbs (or balloon, etc.) are deployed and the antegrade cannula is engaged. The antegrade cannula is then withdrawn along the guided path (or tunnel) and removed from the patient. After the antegrade cannula is withdrawn, the retrograde cannula can be safely withdrawn.

While the present disclosure has been described with a single intermediate opening and elbow socket, there may be a plurality of openings and elbows at different axial locations along the retrograde cannula 102 which may be selectable by the surgeon at the time of surgery, to provide flexibility in the axial location of the opening. In that case, the surgeon may select which opening to use based on the target vessel characteristics.

Also, the design and shape of the elbow 111 FIGS. 1C-1G may be any desired shape and length that provides the desired function and performance, and may have a longer channel 120 to allow for a larger turning radius to reduce the risk of kinking the antegrade cannula or make it easier to deploy the antegrade introducer into the target vessel. For example, it may be disposed circumferentially or spirally along an inner side wall of the retrograde cannula or may protrude further into the flow of the retrograde cannula. In those cases, the cut-out in the retrograde cannula may need to be larger or wider to accommodate for such an elbow path.

Advantageously, the systems and methods according to the present disclosure have the potential to revolutionize advanced life support and cardiothoracic surgery by addressing a significant unmet need with a simple and eminently deliverable design. The systems and methods of the disclosure may significantly reduce, if not eliminate, one of the most severe and prevalent complications associated with peripheral cardiopulmonary bypass. The innovations shown and described herein have the potential to make a profound impact in the field and on the lives of those who would suffer from catastrophic complications attributable to conventional technologies and methods.

Advantageously, the systems and methods according to the present disclosure provides for adequate bi-directional fluid injection in a fluid channel through one entry site. For example, through a single arterial or venous puncture site. By achieving adequate bi-directional fluid injection through a single entry site, unnecessary complications associated with multiple site access can be avoided and the time required to initiate a bypass may be reduced.

Advantageously, the systems and methods according to the present disclosure may prevent or mitigate limb ischemia by allowing for bi-directional blood flow such that the majority of oxygenated blood will travel towards vital organs through a retrograde cannula (or catheter) and at the same time a predetermined small volume will be diverted towards the limb through an antegrade cannula (or catheter). Also, the present disclosure reduces the length of tubing required to deliver oxygenated flow into the limb.

It should be understood that, unless otherwise explicitly or implicitly indicated herein, any of the features, functions, characteristics, alternatives or modifications described regarding a particular embodiment herein may also be applied, used, or incorporated with any other embodiment described herein. Also, the drawings herein are not drawn to scale, unless indicated otherwise.

Conditional language, such as, among others, "can," "could," "might," or "may," unless specifically stated otherwise, or otherwise understood within the context as used, is generally intended to convey that certain embodiments could include, but do not require, certain features, elements, or steps.

Although the invention has been described and illustrated with respect to exemplary embodiments thereof, the foregoing and various other additions and omissions may be made therein and thereto without departing from the spirit and scope of the present disclosure.

What is claimed is at least:

1. A bi-directional fluid injection system comprising:
a retrograde introducer;
a retrograde cannula having an inlet opening, intermediate opening and outlet opening;
an antegrade introducer;
an antegrade cannula;
wherein the retrograde introducer is configured to engage with the retrograde cannula and, when engaged and moved, is configured to insert the retrograde cannula into a fluid channel; and
wherein the antegrade introducer is configured to engage with the antegrade cannula and, when engaged and moved, is configured to insert the antegrade cannula into the fluid channel from within the retrograde cannula through the intermediate opening wherein the retrograde introducer has a receiving opening, and wherein the receiving opening is configured to receive the antegrade introducer and antegrade cannula.

2. The bi-directional fluid injection system according to claim 1, wherein the antegrade introducer is configured to be removed from the antegrade cannula, retrograde introducer and retrograde cannula such that the antegrade cannula remains in the fluid channel, and wherein the retrograde introducer is configured to be removed from the retrograde cannula such that the retrograde cannula remains in the fluid channel.

3. The bi-directional fluid injection system according to claim 2, wherein when the antegrade introducer and retrograde introducer are removed, the retrograde cannula extends in a first direction within the fluid channel and the antegrade cannula extends in a second direction within the fluid channel.

4. The bi-directional fluid injection system according to claim 3, wherein the first direction and the second direction are substantially opposite.

5. The bi-directional fluid injection system according to claim 3, wherein the relative angle between the first direction and the second direction is in the range of 90°-180°.

6. The bi-directional fluid injection system according to claim 5, wherein the relative angle between the first direction and the second direction is in the range of 120°-180°.

7. The bi-directional fluid injection system according to claim 1, wherein the retrograde cannula comprises an elbow socket fluidly connected to the intermediate opening, and wherein the antegrade cannula is configured to form a fluidic seal with a seat of the elbow socket such that fluid may not flow between an exterior surface of the antegrade cannula and an interior surface of the elbow socket and then through the intermediate opening into the fluid channel.

8. The bi-directional fluid injection system according to claim 1, wherein the retrograde introducer has a cut-out.

9. The bi-directional fluid injection system according to claim 1, wherein the antegrade introducer comprises a mounting segment to engage with the antegrade cannula.

10. The bi-directional fluid injection system according to claim 9, wherein the mounting segment comprises a balloon.

11. A method of operating a bi-directional fluid injection system, the bi-directional fluid injection system comprising a retrograde introducer, a retrograde cannula defining an inlet opening, intermediate opening and outlet opening, an antegrade introducer and an antegrade cannula, wherein the retrograde introducer has a receiving opening, and wherein the receiving opening is configured to receive the antegrade introducer and antegrade cannula, the method comprising the steps of: inserting the retrograde introducer while engaged with the retrograde cannula into a fluid channel
    inserting the antegrade introducer while engaged with the antegrade cannula into a receiving opening of the retrograde introducer;
    moving the antegrade introducer and the antegrade cannula so that the antegrade introducer and antegrade cannula protrude into the fluid channel from the retrograde cannula from the intermediate opening;
    disengaging the antegrade introducer from the antegrade cannula;
    removing the antegrade introducer from the antegrade cannula, retrograde introducer and retrograde cannula such that the antegrade cannula remains in the fluid channel;
    disengaging the retrograde introducer from the retrograde cannula;
    removing the retrograde introducer from the retrograde cannula such that the retrograde cannula remains in the fluid channel; and
    wherein when the retrograde introducer and the antegrade introducer are removed from the retrograde cannula and the antegrade cannula, the retrograde cannula extends in a first direction within the fluid channel and the antegrade cannula extends in a second direction within the fluid channel.

12. The method according to claim 11, wherein the first direction and the second direction are substantially opposite.

13. The method according to claim 11, wherein the relative angle between the first direction and the second direction is in the range of 90°-180°.

14. The method according to claim 13, wherein the relative angle between the first direction and the second direction is in the range of 120°-180°.

15. The method according to claim 14, wherein the relative angle between the first direction and the second direction is in the range of 150°-180°.

16. The method according to claim 11, further comprising the step of connecting an inlet opening of the retrograde cannula to a heart-lung machine.

\* \* \* \* \*